United States Patent [19]

Lehn

[11] 4,156,683

[45] May 29, 1979

[54] COMPLEXES OF MACROCYCLIC COMPOUNDS

[75] Inventor: Jean-Marie Lehn, Strasbourg, France

[73] Assignee: Schering Corporation, Kenilworth, N.J.

[21] Appl. No.: 560,280

[22] Filed: Mar. 20, 1975

Related U.S. Application Data

[63] Continuation-in-part of Ser. No. 344,682, Mar. 26, 1973, Pat. No. 3,888,877, which is a continuation-in-part of Ser. No. 43,979, Jun. 5, 1970, abandoned.

[51] Int. Cl.$^2$ ............... C07D 291/02; C07D 291/08; C07D 498/08; C07D 515/08; C07D 513/08; C07D 285/00; C07D 273/00
[52] U.S. Cl. ............................... 260/338; 260/340.3; 260/327 R; 260/239 BC; 424/244
[58] Field of Search ............... 260/338, 340.3, 327 R, 260/239 BC

[56] References Cited

U.S. PATENT DOCUMENTS

| | | | |
|---|---|---|---|
| 3,562,295 | 2/1971 | Pedersen | 260/338 |
| 3,686,225 | 8/1972 | Pedersen | 260/340.3 |

OTHER PUBLICATIONS

Kirk–Othmer Encyclopedia of Chemical Technology, 2nd ed., vol. 6, John Wiley & Sons, Inc., N.Y., 1965, pp. 4 and 5.

*Primary Examiner*—Norma S. Milestone
*Attorney, Agent, or Firm*—Mary S. King

[57] ABSTRACT

Novel macrocyclic (monocyclic and bicyclic) compounds having nitrogen bridgehead atoms and having in the hydrocarbon bridging chains at least two additional hetero atoms selected from the group consisting of sulfur, oxygen, and nitrogen, when admixed with a compatible cation-donor compound form stable cation-containing macrocyclic complexes which, in turn, can be conveniently dissociated by addition of acid or a quaternizing agent. The novel macrocyclics are valuable for use in the same way and for the same purposes as chelating agents.

42 Claims, No Drawings

COMPLEXES OF MACROCYCLIC COMPOUNDS

CROSS REFERENCE TO RELATED APPLICATIONS

This application is a continuation-in-part of co-pending application U.S. Ser. No. 344,682, now U.S. Pat. No. 3,888,877 in turn a continuation-in-part of U.S. Ser. No. 43,979 filed June 5, 1970, now abandoned.

BACKGROUND OF INVENTION

This invention relates to novel compositions-of-matter and to processes for their preparation.

More specifically, this invention relates to compositions of matter which may be classified as macrocyclic compounds and to complexes of said macrocyclic compounds, to methods for their manufacture, and to intermediates produced thereby.

In particular, this invention relates to compositions of matter which may be classified as diaza-macrocyclic compounds and to cation-containing-complexes of said macrocyclic compounds, including methods for their manufacture, and intermediates produced thereby.

SUMMARY OF INVENTION

The invention sought to be patented in the composition-of-matter aspect of my invention resides in the concept of a chemical compound having a molecular structure comprising a hetero-macrocyclic nucleus having nitrogen bridgehead atoms separated by at least two, and preferably three, hydrocarbon bridges, each bridge having at least three adjoining atoms, at least one of said bridges having hydrocarbon radicals separated at intervals by hetero-substituents of the group consisting of oxygen, sulfur, and amino, there being at least two hetero substituents in said macrocyclic nucleus in addition to the nitrogen bridgehead atoms, and when said macrocyclic nucleus is a monocyclic structure, of said two hetero substituents, one is either oxygen or sulfur and the other is either oxygen or amino. The novel macrocyclic compounds of this invention possess the ability to form stable complexes with compatible cation-containing compounds which renders them of value for use in much the same way and for the same purposes as chelating agents. My macrocyclic compounds are particularly valuable for use in processes and methods requiring the separation, withdrawal, or binding of specific cations from a mixture which may include other cations, and in the preparation of cation-containing macrocyclic complex reagents which reagents may also be used in liquid media in which the cation containing compound per se is normally insoluble.

Novel macrocyclic compounds of my invention also demonstrate pharmacological activity.

Preferred species of my invention include bicyclic macrocyclic compounds (i.e. those having three bridging chains) which in general form complexes of greater stability than do the monocyclic macrocyclics of this invention (i.e. those having two bridging chains). Particularly valuable species of the foregoing are the diaza-bicyclo-macrocyclic compounds wherein the bridging chains are polyethers, particularly ethyleneoxy polyethers.

In addition to the above-described macrocyclic compounds and cation-containing complexes thereof, included within the composition of matter aspect of my invention are the amine nitrogen oxides of my bicyclic macrocyclic compounds. These tertiary amine N-oxides (hereinafter called N-oxides) do not form complexes with cation-containing compounds. Additionally, included within my inventive concept are the acid addition salts and quaternary salts of the macrocyclic compounds, which salts also do not form complexes with cation-containing compounds. These salts and N-oxides are thus useful in processes or methods utilizing the macrocyclic complexes of my invention to effect release of the cation from the macrocyclic complex after completion of said process or method.

The invention sought to be patented in a process aspect resides in the concept of preparing a cation-containing macrocyclic complex of this invention by the process comprising admixing a cation-containing compound with a macrocyclic compound of this invention having nitrogen bridgehead atoms unsubstituted by acid addition salts, quaternary salts or N-oxides. A preferred species of this invention is that wherein the cation-containing compound is an inorganic salt.

The invention sought to be patented in yet another process aspect of this invention resides in the concept of dissociating a macrocyclic cation-containing complex of this invention to a cation-free macrocyclic compound of this invention which comprises treating a macrocyclic cation-containing complex with a member of the group consisting of an acid, including Lewis acids, a quaternizing agent and, when dissociating a bicyclic macrocyclic cation-containing complex, an N-oxide forming oxidizing agent, usually a peracid.

General Description of Invention Macrocyclic Compounds

Included within the physical embodiments of the composition of matter aspect of my invention are macrocyclic compounds selected from the group consisting of compounds of following formula I:

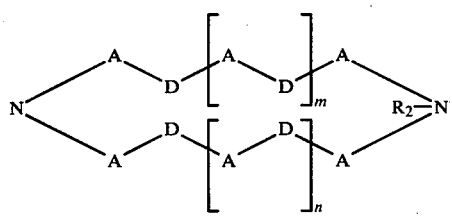

$R_1$ and $R_2$ are members selected from the group consisting of hydrogen, a hydrocarbon radical having up to 12 carbon atoms, and together $R_1$ and $R_2$ form a grouping of the following formula II;

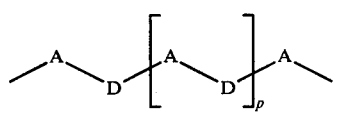

wherein
each A is hydrocarbon radical having up to 12 carbon atoms;
each D is a member selected from the group consisting of oxygen, sulfur, a hydrocarbon radical having up to 12 carbon atoms, and =N—R (R being a member selected from the group consisting of hydrogen, a hydrocarbon radical having up to 12 carbon atoms, a hydrocarbonsulfonyl radical having up to 12 carbon atoms, a lower alkoxycarbonyl radical, a lower alkoxycarbonyl-methylene radical and a carboxymethylene radical); at least two of said D members being heterosubstituents selected from the group consisting of oxygen, sulfur and =N—R; and when each of $R_1$ and $R_2$ are members selected from the group consisting of hydrogen, and a hydrocarbon radical, one of said two hetero substituents is selected from the group consisting of oxygen and sulfur, the other of said two hetero substitutents is selected from the group consisting of oxygen and =N—R;

m, n, and p are integers from 0 to 5;

and cation-containing-complexes of compounds of formula I;

and N-oxides of formula I when $R_1$ and $R_2$ together form a grouping of above formula II;

and ammonium quaternary salts and acid addition salts of compounds of formula I.

The hydrocarbon groups represented by A and D usually have from 2 to 12 carbon atoms, although those having a greater number of carbon atoms are also contemplated as within the scope of this invention. The radicals A and D usually have less than six directly connecting carbon atoms in the bridging chain, ethylene and substituted ethylene groups being particularly preferred. Among the preferred groups for A and D are: straight and branched chained alkylene and alkenylene groups having from 2 to 8 carbon atoms such as ethylene, propylene, butylene, pentylene, hexylene and octylene and their unsaturated analogs; cycloalkylene and cycloalkenylene groups such as cyclopropylene, cyclobutylene, cyclopentylene, cyclohexylene and cycloheptylene and their unsaturated analogs; the corresponding cycloalkylene-di-alkyl groups such as cyclohexylene-dimethyl and aromatic groups such as phenylene and phenylene-di-alkyl, preferably phenylene-di-methyl. The groupings A which are adjacent to $N_1$ and $N_2$ preferably have analiphatic moiety attached to $N_1$ and $N_2$.

The hydrocarbon groups represented by R, $R_1$ and $R_2$ usually have from 1 to 12 carbon atoms. Preferred are straight and branched alkyl groups having from 1 to 8 carbon atoms usually 1 to 4 carbon atoms and straight or branched alkenyl groups having from 2 to 8 carbon atoms. Other typical representatives are cycloalkyl, aralkyl and aryl groups.

The =N-hydrocarbonsulfonyl groups contemplated for the substituent D are preferably those derived from aryl hydrocarbonsulfonic acids having up to 12 carbon atoms, e.g. from benzenesulfonic acid, xylylsulfonic acid, naphthalenesulfonic acid, and, preferably from p-toluenesulfonic acid.

Among the =N-lower alkoxycarbonyl and =N-lower alkoxycarbonylmethylene groups contemplated for the substituent "D" (i.e. =N—COOR' and =N-CH$_2$COOR', also identified as =N-carbalkoxy and =N-methylenecarbalkoxy), preferred are those wherein R' is methyl or ethyl.

Of the =N—R groups contemplated for the substituent D, useful compounds include those wherein R is hydrogen or a hydrocarbon radical having up to 12 carbon atoms.

The hetero-macrocyclic compounds of this invention are named in accordance with the International Union of Pure and Applied Chemistry 1957 Rules (i.e. the IUPAC 1957 Rules) such as set forth in the J. Am. Chem. Soc. 82, 5545 (1960). Thus, for example, the following monocyclic and bicyclic structures are named as indicated hereinbelow:

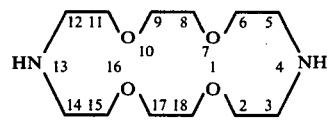

1, 7, 10, 16-tetra oxa-4, 13-diazacyclooctadecane

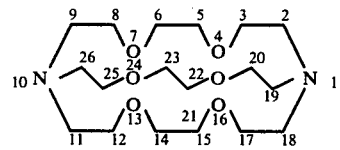

4, 7, 13, 16, 21, 24-hexa oxa-1,10-diazabicyclo-[8,8,8]hexacosane.

In accordance with established custom, when structural formulae such as those set forth hereinabove are used in the specification and claims of this application, it is understood that methylene groups (i.e. —CH$_2$—) are present at every point in the structure where two lines meet at an angle.

Preferred compounds of this invention are bicyclic macrocyclic compounds in which m, n and p are integers from 0 to 3, particularly those compounds wherein m, n and p are integers from 0 to 2. Of these, those compounds wherein D is oxygen or sulfur are particularly valuable as complexing agents as described hereinbelow, a particularly valuable species being diaza-bicyclo-macrocyclic compounds wherein the bridging chains are polyethers, particularly ethyleneoxypolyethers. Listed below are typical configurations of preferred compounds of my invention.

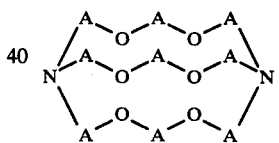

1.

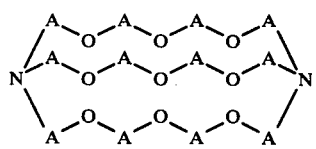

2.

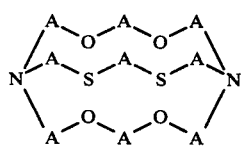

3.

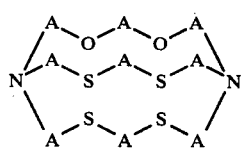

4.

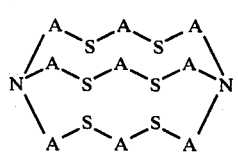

5.

6.
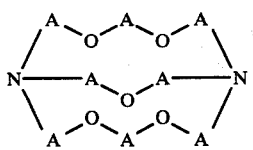

7.
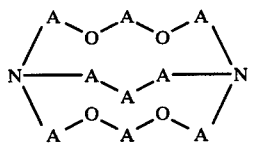

8.
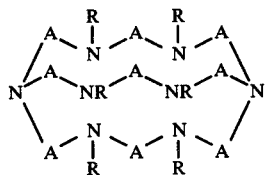

9.
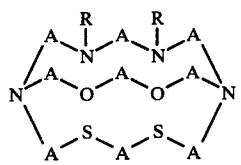

10.
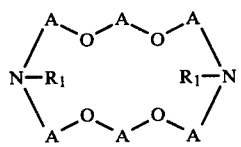

11.
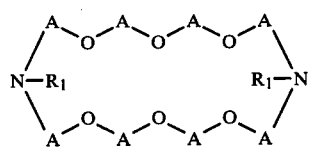

12.
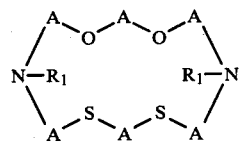

13.
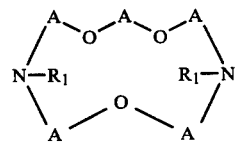

14.
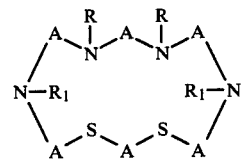

15.
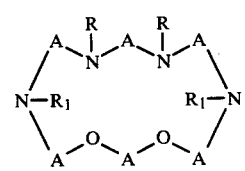

16.
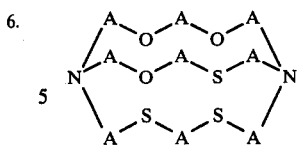

The typical representatives of the compounds of this invention may be illustrated by inserting various groups for A and $R_1$ in the above formulae:

| | |
|---|---|
| A = $-CH_2-CHR''-$ | (i) |
| A = $-CH_2-CHR''-CH_2-$ or $-CHR''-CH_2-CH_2-$ | (ii) |
| A = (cyclohexyl with R'') | (iii) |
| A = (cyclohexyl with R'', $-CH_2-\cdots-CH_2-$) | (iv) |
| A = unsaturated analogs of the groupings (i) to (iv) | (v) |
| A = (phenyl with R'') | (vi) |
| A = (phenyl with R'', $-CH_2-\cdots-CH_2-$) | (vii) |
| $R_1 = -CH_3$; $-CH_2-CH_2R''$; $-CH_2-CH_2R''-CH_3$; and unsaturated analogs | (viii) |
| $R_1 = -CH_2-$(phenyl with R'') | (ix) |
| $R_1 = -$(phenyl with R'') | (x) |
| $R_1 = H$ | (xi) | wherein R'' is hydrogen or a hydrocarbon radical having up to 12 carbon atoms.

The ammonium quaternary salts and acid addition salts may be illustrated by the following general formulae:

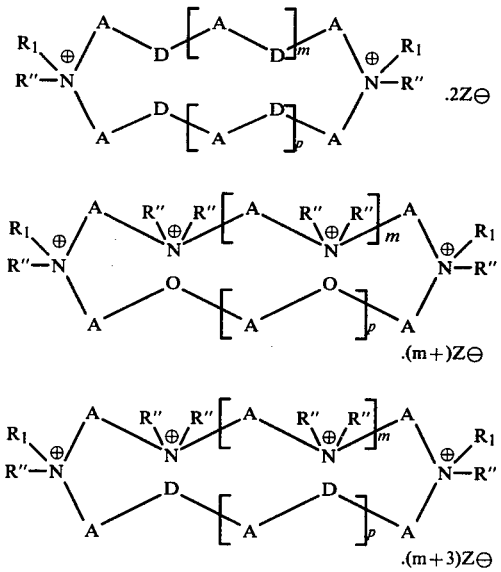

.2Z⊖

.(m+)Z⊖

.(m+3)Z⊖ wherein A, D, R'', R₁, m and p are as previously defined and Z is an inorganic or organic anion, the acid addition salts being illustrated by those compounds wherein R'' is hydrogen and the quaternary salts being illustrated by those compounds wherein R'' is a hydrocarbon radical. It is obvious to one skilled in the art that several other configurations are possible.

Process of Preparing Macrocyclic Compounds

The macrocyclic compounds of this invention may be prepared by using procedures analogous to known chemical reactions. The principle of the processes is to introduce a further bridge into a starting compound having one or two bridges, whereby the desired mono or bicyclic compounds are obtained.

A suitable process for the preparation of the compounds of this invention is characterized in that a compound of the general formula III

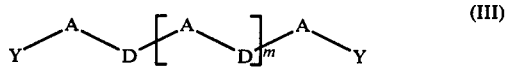
(III)

is condensed with a compound of the general formula IV

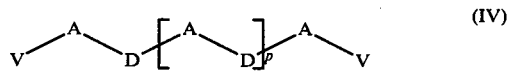
(IV)

whereby in the above formulae A, D, m and p are as previously defined and either V is halogen or other good leaving group such as methanesulfonate and p-toluenesulfonate and Y is selected from the groupings

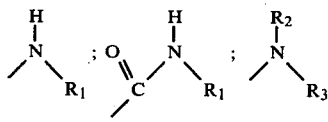

$R_1$ and $R_2$ being as previously defined, $R_3$ being an hydrogenolysable group; or V is the grouping

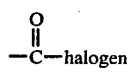

and Y is the grouping

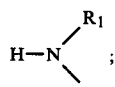

that any carbonyl group in a so-obtained compound is reduced to $CH_2$; and that, if desired, a compound obtained by any of the previous steps is subjected to one or more of the following finishing steps:

(a) hydrogenolysation of hydrogenolysable groups represented by $R_2$ and/or $R_3$;

(b) transformation into an ammonium salt;

(c) transformation into a tertiary amine nitrogen oxide (i.e. to an N-oxide).

Usually, the most preferred halogen atom in the above reaction is bromine, although under certain conditions intermediates wherein the halogen is chlorine or iodine are advantageously employed; and the preferred hydrogenolysable group is the benzyl group. Other examples of hydrogenolysable groups are —$CH_2OH$, —$CH_2$—$CH=CH_2$ and —$CH_2$—$CH_2$—$CN$.

Various embodiments of the above process may be illustrated by the reaction schemes A to H below wherein the starting compounds are known in the art or prepared according to procedures known in the art.

Of the following, reaction schemes B, D, F and G exemplify one process aspect of this invention and is the method usually employed when preparing the diazamacrocyclic compounds of this invention. Reaction schemes A, C, E and H exemplify another process aspect of this invention.

A:

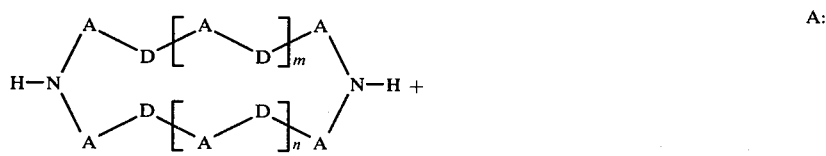

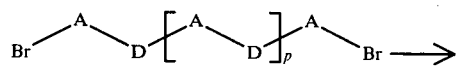

-continued
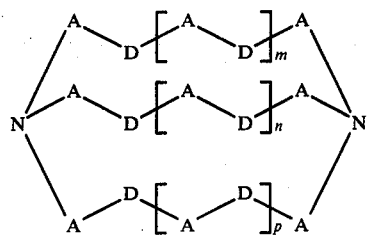
B:
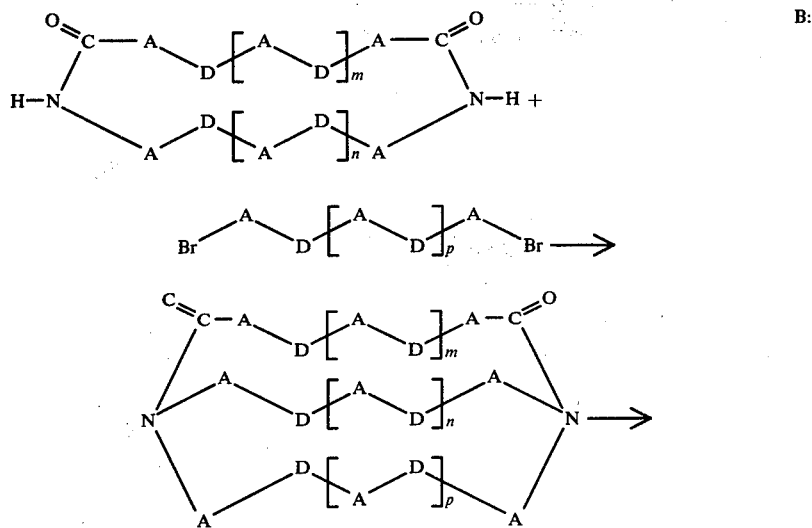
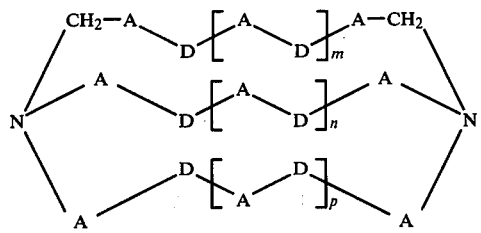
C:
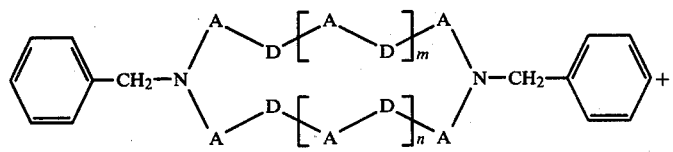
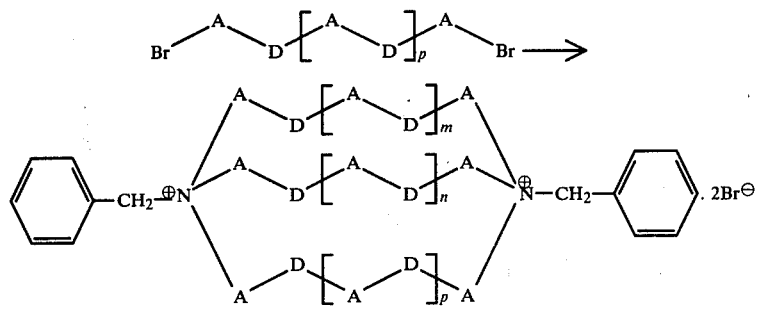
D:
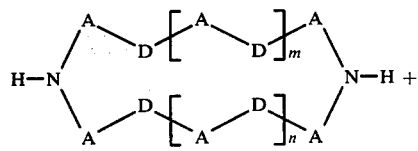

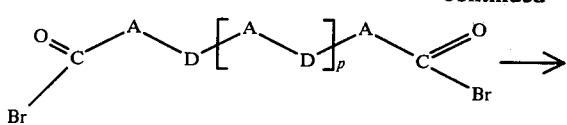
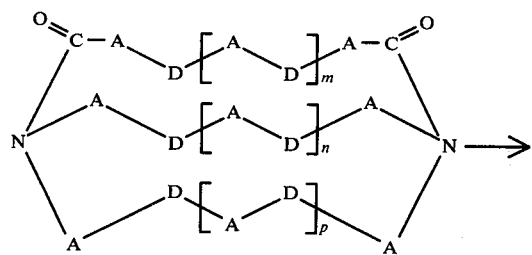
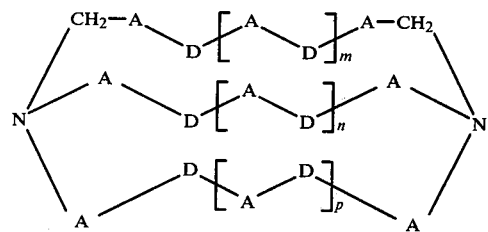
E:
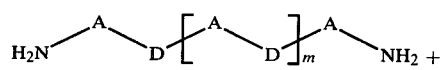
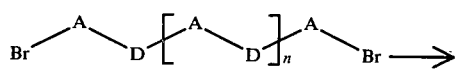
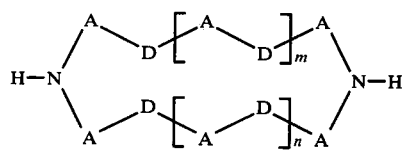
F:
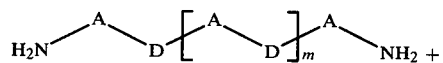
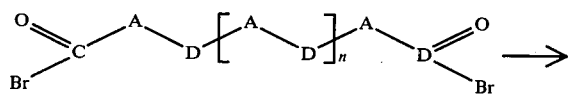
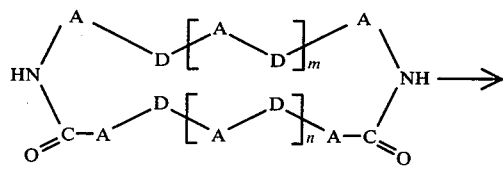
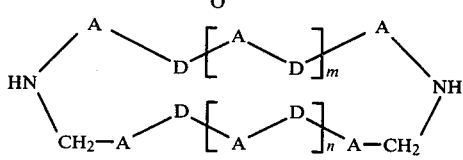
G:
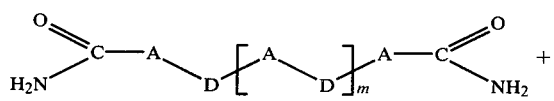
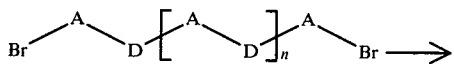

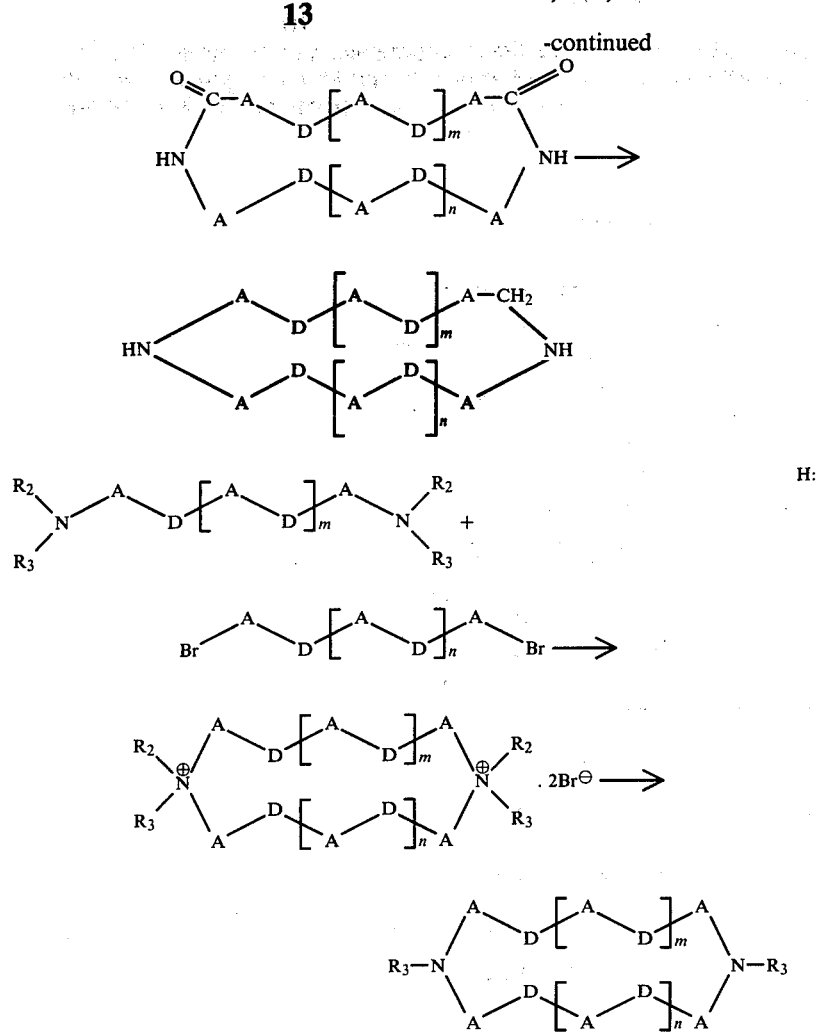

H:

In order to prevent the formation of polymers, the condensation in the first step of the above-described reactions is carried out using high dilution techniques. Any inert solvent may be used, but benzene, toluene and dioxane are preferred. The acid formed during the reaction must be neutralized. This may be accomplished by using two moles of the diamine to each mole of the halide, or by adding a further base, particularly a tertiary amine such as trialkylamine or pyridine, preferably triethylamine.

The reduction of the carbonyl groups in the second step of the reactions B, D, F and G is preferably carried out by means of $LiAlH_4$ or $Al_2H_6$ or $B_2H_6$ in tetrahydrofurane. Other possible reducing agents are mixed metal hydrides such as for example $NaBH_4$, $LiAlH_3$-$OCH_3$, $LiAlH_4/AlCl_3$ and $NaBH_4/BF_3$.

For the preparation of cyclic lactam according to the process indicated in reactions B and G preferably the disalt of the amide group, preferably the alkali metal, is used.

The transformation of a compound of formula I into an ammonium quaternary salt or acid addition salt may be accomplished by using standard methods such as reaction with a suitable quaternizing agent or an acid; for example, with an alkyl halide (e.g. methyl iodide) or with a hydrogen-halide (e.g. hydrogen chloride) respectively.

Similarly any hydrogenolysable groups may be removed by using standard techniques such as catalytical or electrolytical reduction. Examples of catalysts which may be used are platinum, palladium, rhodium, ruthenium and preferably, $LiAlH_4$. Thus the immediate product of reaction scheme C (an ammonium salt) may, if desired, subsequently be transformed into the free macrocycle by reduction in presence of $LiAlH_4$ or $Al_2H_4$.

Also, the transformation of a bicyclic compound of formula I into its tertiary amine nitrogen oxide may be accomplished by applying standard oxidation procedures such as treatment with excess dilute hydrogen peroxide in water or with peracids, e.g. perphthalic acid in ether.

Often the immediate product of the above reaction is not the free macrocyclic compound but rather a derivative thereof additionally containing part or all of the structural elements of other constituents of the reaction mixture; in such a case, the macrocyclic compound is subsequently liberated from such derivative, by standard procedures such as for example treatment with dilute acid whereby the acid addition salt of the macrocycle is formed, or with other hydrolyzing agents.

Any such salt may be dissolved in water and treated with an anion exchange resin. The so-obtained aqueous solution of the free macrocycle may then be isolated by evaporation to dryness.

For the preparation of those compounds in which $R_1$ is a hydrocarbon, it is also possible to use a starting compound of formula III in which $R_1$ in the definition of Y is hydrogen, and to introduce the desired substituents at any stage of the process. The introduction of these substituents may be accomplished by means of known methods.

Thus, as an example, the 4,13-dimethyl-1,7,10,16-tetraoxa-4,13-diaza-cyclooctadecane may be obtained according to the following reaction schemes:

The starting compounds of the general formulae III and IV may be obtained according to known methods. Some of the most convenient methods are illustrated by

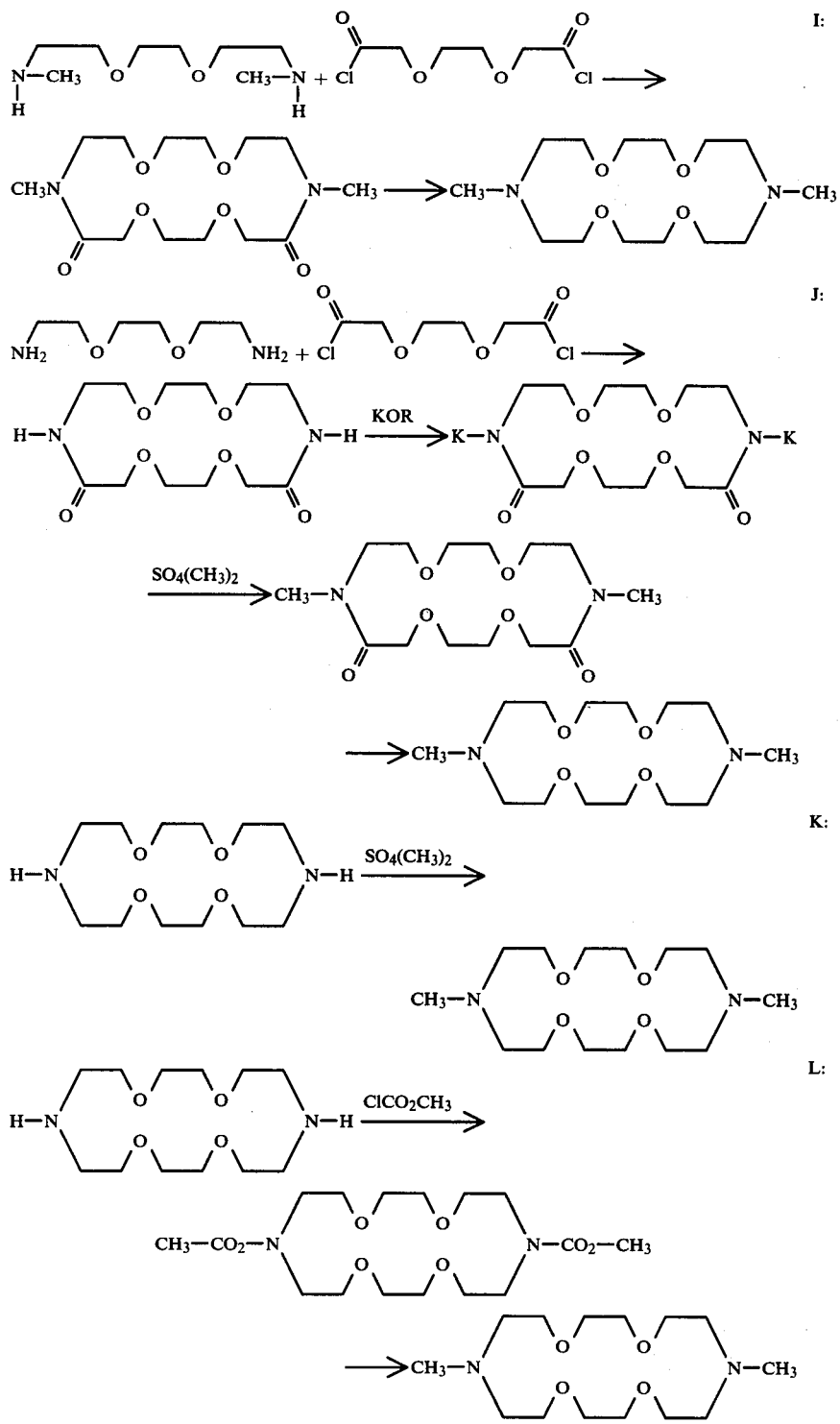

In the above reactions the reagents mentioned may be replaced by any other suitable reagents. If the methylation agents or reagents are replaced by other alkylating agents, compounds in which $R_1$ represents higher hydrocarbon groups are obtained.

The compounds in which $R_1$ represents alkenyl groups may be obtained following the same procedures.

Examples.

Cation-Containing Macrocyclic Complexes and Process for Their Preparation

The macrocyclic compounds of formula I are readily soluble in most common organic solvents and in water.

The novel macrocyclic compounds have an unusual ability to form stable complexes with compatible cations. In the monocyclic compounds, i.e. those compounds of formula I in which $R_1$ and $R_2$ are hydrogen, alkyl or alkenyl, the cation presumably is held in the center of the macrocycle. In the bicyclic compounds, i.e. those compounds of formula I wherein both $R_1$ and $R_2$ together form a third bridge between the two nitrogen atoms, the bridges between the two nitrogen atoms probably form a "cage" in which the cation is situated. The ability to form complexes and the stability of the complexes formed seem to depend on the arrangement of the hetero atoms or groups surrounding the cation and on the relative diameters of the ring(s) and the cation. Complexes of the monocyclic compounds are much less stable than the complexes formed from the same cation with bicyclic compounds and macrocyclic compounds forming stable complexes with cations of a certain diameter are not able to form complexes with cations having much larger diameters.

Each macrocyclic molecule is able to form a complex with a single cation. The magnitude of the charge on the cation has no influence on complex formation. The cations may be inorganic or organic. The larger macrocyclic compounds of this invention may also form polycation (e.g. di-cation) complexes with cations of smaller diameter as well as forming a complex with a single cation of larger diameter.

The cation-containing complexes formed are generally readily soluble in water, $CHCl_3$, $CH_2Cl_2$, and in acetone or other polar solvents, whereas they are slightly soluble or essentially insoluble in non polar organic solvents. They dissociate at an acid pH. Protonation of the free diamine hinders complex formation and leads to the dissociation of the complex by displacement of the equilibrium. The same dissociation is accomplished by treatment with an acid, including Lewis acids. Release of the cation may also be accomplished by treating the complex with a quaternizing agent. Dissociation of a complex of a bicyclic macrocyclic compound may also be effected by treatment with a peracid, e.g. m-chloroperbenzoic acid, to obtain an N-oxide derivative of formula I.

The cation-containing macrocyclic complexes are normally formed by dissolving the macrocyclic compound and the cation yielding compound in a common solvent, such as for example acetone, methanol or water. The mixture normally is heated approximately to the boiling point of the solvent. If the complex formed is insoluble in the solvent used, the complex will crystallize and may be separated by filtration. If the complex formed is soluble in the solvent used, it may be isolated by evaporating the solution to dryness. The complexes may be purified by recrystallization.

Complexes may also be formed when the cation yielding compound (e.g. the salt) is insoluble in the solvent used. It is sufficient to bring a solution of the macrocyclic compound together with the ctystalline salt and agitate the mixture with or without heating.

The formation of complexes is possible even if the cation yielding compound and the macrocyclic compound are poorly soluble in the medium used. In this case, the macrocycle and the cation yielding compound are mixed in the presence of a medium which is then agitated and heated, whereby the crystalline macrocycle gradually changes into the crystalline cation-containing macrocyclic complex.

The presence of a complex in solution can be determined by spectroscopic analysis, as the addition of the cation causes changes in the spectral patterns of the macrocycle in solution.

The novel cation-containing macrocyclic complexes make it possible to use certain chemical reagents in solvents in which they are normally insoluble. For example potassium fluoride is insoluble in chloroform, whereas a complex of the salt with 4,7,13,16,21,24-hexaoxa-1,10-diazabicyclo[8,8,8]hexacosane is readily soluble in chloroform.

The cation complexing properties of the macrocyclic compounds of this invention make them of value for use in much the same way and for the same purposes as chelating agents. Thus, the cation complexing properties of the macrocyclic compounds render them of value in processes directed to the desalination of brines or to the separation of metals, for example to the separation of metals such as the transition metals and the actinides from low grade sources of these metals and to subseqently obtaining such metals in high purity form. In this connection, the macrocyclic compounds are considered to be particularly useful in the separation of high cost metals such as those of the platinum group. In the separation of uranium from treated ores, the uranium may be complexed with the macrocycle compound and the resulting cation-containing macrocyclic complex subsequently separated by water. Treatment of the uranium-macrocyclic complex with acid will then release the uranium from the complex in the form of a uranium salt.

The macrocyclic compounds of the invention may also advantageously be used for cation transport and for the preparation of ion selective membranes and electrodes.

The macrocyclic compounds are also of use in chemical syntheses, e.g. in polypeptide and protein syntheses, wherein the marcocyclic compounds advantageously selectively protect one of the ammonium cation groups in the amino acid. Additionally, the macrocylic compounds may be used as catalysts for ionic reactions in a polar organic media wherein the macrocyclic compounds activate the reaction via an "agent-separated ion pair" mechanism. Thus, for example, the potassium hydroxide complex of 4, 7, 13, 16, 21, 24-hexaoxa-1,10-diazabicyclo[8,8,8]hexacosane in tetrahydrofuran (prepared as described in Example 46) is a useful catalyst for reactions requiring strongly basic conditions. Thus, when five grams of fluorene are added to a tetrahydrofuran solution of 50 mgm. of the aforementioned potassium hydroxide complex of Example 46, the fluorene is converted to the fluorenyl anion (as evidenced by a strong red color) as water is concomitantly formed from the fluorene proton and the hydroxide anion of the potassium hydroxide macrocyclic complex.

By bubbling oxygen through this solution, the fluorene (in the form of the fluorenyl anion) is converted to fluorenone and the potassium hydroxide-macrocyclic complex is regenerated. This reaction (which illustrates a catalytic ratio of 1:200) may be shown diagramatically as follows wherein M is the macrocyclic 4, 7, 13, 16, 21, 24-hexaoxa-1, 10-diaza bicyclo [8,8,8] hexacosane.

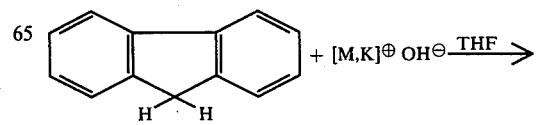

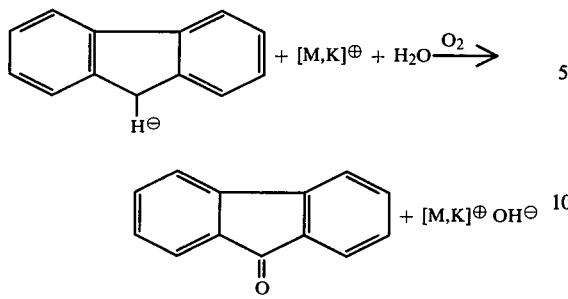

When administered to an animal, e.g. mammals, the macrocyclic compounds have an action on biological cation mechanisms such as nervous conduction, sodium-potassium pump, and calcium metabolism of muscle and bone. These compounds are thus useful in conditions in animals requiring the regulation of cation exchange within the host.

In addition to the foregoing, macrocyclic compounds of this invention have been found to possess pharmacological activity. For example, the N-alkylated compounds of the invention, e.g. 4,13-dimethyl-1,7,10,16-tetraoxa-4,13-diazacyclooctadecane, demonstrate antiviral activity against $A_2$ influenza when measured by a modification of the well recognized in vitro methods of Hermann in chick fibroblast tussue culture.

Additionally, the bicyclic macrocyclic compounds of this invention, e.g. 4,7,13,16,21,24-hexaoxa-1,10-diazaicyclo[8,8,8] hexacosane, have been found to inhibit catechol amine induced free fatty acid mobilization when tested in vitro with isolated adipose tissue. These compounds are therefore of use in the treatment of diabetes and hyperlipemia.

It is apparent from the foregoing that the ability of the macrocyclic compounds of my invention to form cation-containing macrocyclic complexes renders them of value for use in a multitude of processes and methods requiring the separation, withdrawal, or binding of specific cations from a mixture which may include other cations. Of particular value in such processes is the ease with which the cation may be dissociated from the cation-containing macrocyclic complex after completion of a process. Simple protonation of the complex by addition of acid will cause dissociation of the complex into the macrocyclic compound per se as the acid salt and a cation donor compound (e.g. a salt). Thus, for example, treatment of the silver chloride complex of 4,7,13,16,21,24-hexaoxa-1,10-diazabicyclo [8,8,8]-hexacosane with hydrochloric acid will release the silver cation from the complex with formation of the hydrochloride salt of the macrocycle and regeneration of silver chloride salt. This may be shown diagrammatically as follows, m being the macrocyclic compound:

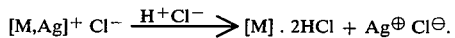

Similarly, treatment of a cation-containing complex with a quaternizing agent, e.g. methyl iodide, will effect release of the cation from the macrocyclic compound with formation of the quaternary salt of the macrocyclic compound and reformation of a cation-containing donor.

Also, treatment of a cation-containing bicyclic macrocyclic complex with a per-acid, e.g. m-chloroperbenzoic acid, will effect release of the cation from the bicyclic macrocyclic compound with formation of the N-oxide salt of the bicyclic macrocyclic compound and roformation of a cation-containing donor.

This process, which is one of the process aspects of my invention whereby a cation is easily released from a cation-containing macrocyclic complex of my invention is thus particularly useful in processes such as in ore separation for the convenient isolation (in the form of a salt) of the ore being mined or purified. A preferred species of this process is that wherein release of the cation is effected by addition of acid to produce an acid addition salt of the macrocyclic compound. Regeneration of the macrocyclic compound per se is easily accomplished by addition of base to a solution of the acid addition salt until the solution is about pH 7.

Additionally, this process provides a convenient means for purifying the macrocyclic compounds of this invention. Thus, a macrocyclic compound prepared according to the processes discussed hereinabove, which is difficult to purify or separate from by-products, may be converted to a cation-containing complex of this invention. Isolation and purification of the complex followed by treatment with acid will yield a purified macrocyclic compound of this invention as the acid addition salt.

As disclosed hereinabove a cation complex of this invention comprises a union of one molecule of a macrocyclic compound with one molecule of a cation-donor compound whereby the cation of said donor compound is held or "trapped" within the macrocyclic compound while the anion of said donor compound is free to move in ionized form when in a liquid ionizing medium. In such ionizing medium, the cation macrocyclic fragment remains together to form a positively charged ion fragment. Although all the variable factors have not yet been determined as described hereinabove, the complexing ability of the macrocyclic compounds varies depending upon the size of the macrocyclic compound, the number and type of hetero atom therein, and the cation-donor compound. A macrocycle of large structure will show strong complexing activity with cations of larger structure, and weaker complexing acitivity with smaller cations which can easily escape the macrocyclic compound "cage". In preparing my macrocyclic bicyclic compounds, the size of the cavity therein can be altered by varying the length of the $(AD)_n$ bridges, thereby providing a better or poorer fit as metallic ion size varies. The equilibrium constant for binding (Ks described hereinbelow) provides a measure of the binding strength of a given macrocycle for a given cation, the negative logarithm thereof (i.e.-$pK_s$) being a convenient method of reporting the binding strength of a given macrocycle for a given cation, the higher the $-pK_s$ value, the stronger the binding properties of the macrocyclic. Listed hereinbelow are data on the binding strength ($-pk_s$) of macrocyclic compounds of our invention and a description of the method whereby such data was obtained.

The binding constant ($-pK_s$) data of the cation-containing complexes of my invention such as that shown hereinbelow provides a convenient means for predicting which macrocyclic compounds of my invention will be preferable over others in a given process. Thus, with reference to the tables set forth under section C hereinbelow it is noted that the macrocyclic compound of Example 6 (a preferred compound of my invention) is useful in separating silver, thallium and lead from treated ores since this compound has high binding constants with silver, thallium and lead cations. It is noted further that one would use the macrocyclic compound of Example 6 in preference to macrocyclic compounds of Example 22 to separate a lead salt from an ore since the binding constant ($-pK_s$) of the former (i.e. $+12.05$) is higher than the binding constant of the latter ($+8.11$).

From tables A(3) and B(3), it is evident that the macrocyclic compound of Example 6 has a binding constant for the potassium cation ($-pK_s = +5.17$) which is less than its binding constant for strontium. The compound of Example 6 is thus useful to effect elimination of freshly incorporated radioactive strontium from a mammal by administering thereto (e.g. by subcutaneous injection) the potassium chloride complex of the compound of Example 6 in physiological solution. Since the macrocycle of Example 6 binds strontium cation more strongly than potassium cation, an ion exchange takes place and there is formed a strontium chloride macrocyclic complex with liberation of the potassium cation. The strontium chloride-macrocyclic complex is then eliminated from the mammal via usual routes. In similar manner the potassium chloride complex of Example 6 can be used to eliminate barium from a mammal since the barium binding constant (9.48) is also much greater than the potassium binding constant (5.17).

Macrocyclic compounds of my invention which bind lithium more strongly than potassium or sodium, e.g. the macrocyclic of Example 55 (see Table A(1) hereinbelow) are also useful in the treatment of lithium intoxication. On the other hand, the macrocyclics of Examples 43 and 6 are not desirable for treating lithium intoxication since these compounds bind potassium and sodium more strongly than lithium (see tables A(2) and A(3) hereinbelow).

Additionally, macrocyclics having a stronger binding constant for sodium than potassium (e.g. the compounds of Examples 55 and 43 (tables A(1) and A(2) ) are useful as naturetic agents.

Similarly, from table A(3) it is evident that the macrocyclic compound of Example 6 has a very low binding constant with cesium cation (i.e. less than 1.5) while having good binding constants with sodium, potassium and rubidium cations (i.e. 3.75, 5.17, and 4.20 respectively). The compound of Example 6 thus provides a convenient method to effect what is now a difficult separation of cesium salts from salts of sodium, potassium and rubidium with which cesium co-occurs in nature. Thus, for example, by adding the compound of Example 6 to a brine containing the aforementioned salt mixture, there are preferentially formed complexes of the compound of Example 6 with the sodium, potassium and rubidium salts, which complex mixture can be extracted from the brine by an organic solvent, for example, leaving behind the cesium salt.

Following are tables listing the stability constants (Ks) and binding constants ($-pK_s$) of typical bicyclic macrocyclic compounds of my invention.

Stability constants of macrocycle complexes in aqueous solution

General

It has been determined by measuring the pH, in water, the equilibrium constants for reactions of the following type, the type being illustrated by bicyclic amine macrocycles:

(1) $A + {}^- \rightleftarrows AM^+$ $K_s = [AM^+]/[A][M^+]$;

where
$K_s = $ law of mass action constant;
$A = $ bicyclic amine under consideration;
$AM^+ = $ macrocycle complex;
$M^+ = $ cation;
$[\ ] = $ activity of the ionic species.

Equilibria present

Complexation
(1) $A + M^+ \rightleftarrows AM^+$ ($K_s$)

$K_s = [AM^+]/[A][M^+]$

Protonation of the diamine (2) $AH_2^{++} \rightleftarrows AH^+ + H^+$ ($K_1$)
(3) $AH^+ \rightleftarrows A + H^+$ ($K_2$ $K_1 = [AH^+]/[AH_2^{++}]$ $K_2 = [A][H^+]/[AH^+]$ Protonation of the macrocycle complex
(4) $AMH_2^{3+} \rightleftarrows AMH^{2+} + H^+$ ($K_1'$)

$AMH^{2\ 30} \rightleftarrows AM^+ + H^+$ ($K_2'$)

$K_1' = [AMH^{++}][H^+]/[AMH_2^{3+}]$ $K_2' = [AM^+][H^+]/AMH^{++}$

It has been verified that the last two equilibria of protonation of the macrocycle complex, remain comparatively neglibible and have established a formula relating $K_s$ to the pH and all constants of the mixture:

$K_s = [(bC_A-aC)/(bC_M-(bC_A-aC))]\cdot(b/C)$ where:
$C = C_H + [OH^-] - [H^+]$
$a = 1 + ([H^+]/K_2) + ([H^+]^2/K_1 K_2)$
$b = ([H^+]/K_2) + (2[H^+]^2)/(K_1 K_2)$
$C_H = $ Concentration of added acid (moles/litre)
$C_A = $ Concentration of the amine, if no reaction took place (moles/litre)
$C_M = $ Concentration of the metal, if no reaction took place (moles/litre) $K_s$ is expressed in moles$^{-1}$. litre
$K_1$ and $K_2$ are preliminarily determined by titrating the diamine with dilute hydrochloric acid, in the presence of a reference salt of known concentration (N $Me_4^+ Br^-$ for the small cages, Li Cl for the large cages).

After addition of a known quantity of the salt to a solution of the amine of known concentration, in the presence of a non-complexed reference salt of the same concentration used for the determination of $K_1$ and $K_2$, the solution is titrated with dilute HCl taking pH measurements of the solutions. Each point of addition provides a value of $K_s$ (by applying the preceding formula). Calculation should provide a value of $K_s$ which is approximately constant throughout the titration.

Results obtained (at 25.0° C. ± 0.2° C.)

(A) Alkali Metals
Compound Ex. 55

1). 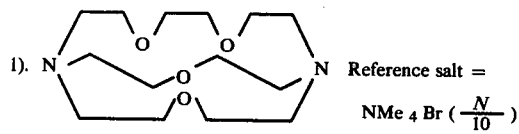 Reference salt = NMe$_4$ Br ($\frac{N}{10}$)

| Cation | $K_s$ | $-pK_s$ | Protonation of the amine |
|---|---|---|---|
| Li$^+$ | 1.5×10$^4$ | 5.5 | $K_1=3.0\times10^{-8}$; $-pK_1=7.52$ |
| Na$^+$ | 5.5×10$^2$ | 3.2 | $K_2=1.2\times10$; $-pK_2=9.92$ |
| K$^+$ | } <10$^{1.5}$ | } <1.5 | $\Delta(pK_s)\simeq0.10$ |
| Rb$^+$ | | | |
| Cs$^+$ | | | |

Compound Ex. 43

2). 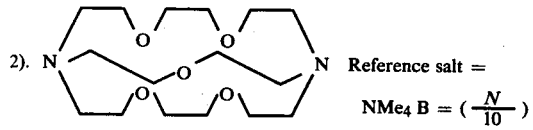 Reference salt = NMe$_4$ B = ($\frac{N}{10}$)

| Cation | $K_s$ | $-pK_s$ | Protonation of the amine |
|---|---|---|---|
| Li$^+$ | 2.7×10$^2$ | 2.43 | $K_1=3.2\times10^{-8}$; $-pK_1=7.50$ |
| Na$^+$ | 1.9×10$^5$ | 5.28 | $K_2=3.0\times10$; $-pK_2=10.52$ |
| K$^+$ | 8.2×10$^3$ | 3.91 | $\Delta(pK_s)\simeq0.10$ |
| Rb$^+$ | 3.-5×10$^2$ | 2.54 | |
| Cs$^+$ | <10$^{1.5}$ | <1.5 | |

Compound Ex. 6

3). 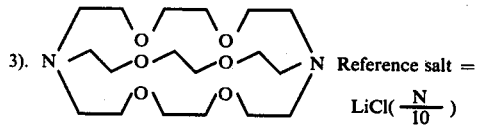 Reference salt = LiCl($\frac{N}{10}$)

| Cation | $K_s$ | $-pK_s$ | Protonation of the amine |
|---|---|---|---|
| Li$^+$ | <10$^{1.5}$ | <1.5 | $K_1=5.2\times10^{-8}$; $-pK_1=7.28$ |
| Na$^+$ | 5.6×10$^3$ | 3.75 | $K_2 2.5\times10^{-10}$; $-pK_2=9.60$ |
| K$^+$ | 1.5×10$^5$ | 5.17 | $\Delta pK_s\simeq0.10$ |
| Rb$^+$ | 1.6×10$^4$ | 4.20 | |
| Cs$^+$ | <10$^{1.5}$ | <1.5 | |

Compound Ex. 22

4) 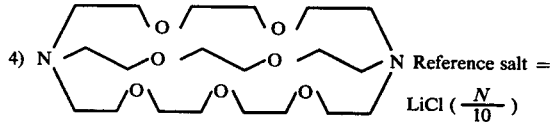 Reference salt = LiCl ($\frac{N}{10}$)

| Cation | $K_s$ | $-pK_s$ | Protonation of the amine |
|---|---|---|---|
| Li$^+$ | | | $K_1=4.7\times10^{-8}$; $-pK_1=7.33$ |
| Na$^+$ } | <10$^{1.5}$ | <1.5 | $K_2=3.2\times10^{-9}$; $-pK_2=8.50$ |
| K$^+$ | | | $\Delta(pK_s)\simeq0.10$ |
| Rb$^+$ | 4×10$^2$ | 2.60 | |
| Cs$^+$ | 1.5×10$^2$ | 2.18 | |

Compound Ex. 24

5). 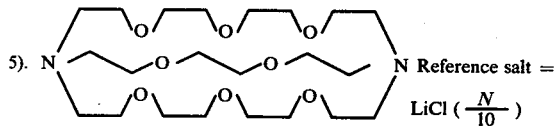 Reference salt = LiCl ($\frac{N}{10}$)

$-pK_1 = 7.31$
$-pK_2 = 8.16$

For Li, Na, K, Rb : $K_s<10^{1.5}$
Cs$^+$ : $K_s\simeq60$  $-pK_s\simeq1.7$  (±0.5)

Compound Ex. 18

6). 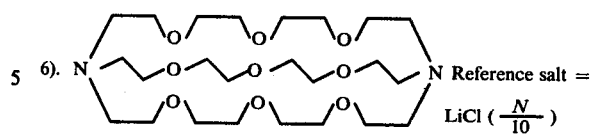 Reference salt = LiCl ($\frac{N}{10}$)

$-pK_1 = 6.96$
$-pK_2 = 7.70$

For the alkali metals $K_s < 10^{1.5}$ (B) Alkaline - Earth Metals

Compound Ex.55

1). 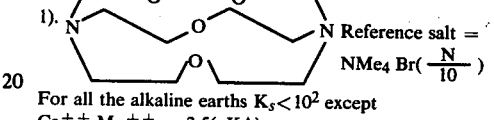 Reference salt = NMe$_4$ Br($\frac{N}{10}$)

For all the alkaline earths $K_s<10^2$ except Ca$^{++}$ Mg$^{++}$ ~ 2.5(pK$\Delta$)

Compound Ex.43

2). 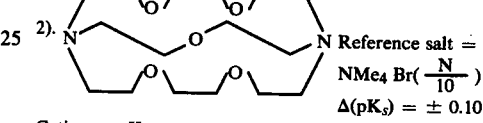 Reference salt = NMe$_4$ Br($\frac{N}{10}$)

$\Delta(pK_s) = \pm 0.10$

| Cation | $K_s$ | $-pK_s$ |
|---|---|---|
| Mg$^{++}$ | <10$^2$ | <2 |
| Ca$^{++}$ | 5.0×10$^6$ | 6.70 |
| Sr$^{++}$ | 1.2×10$^7$ | 7.07 |
| Ba$^{++}$ | | |

Compound Ex.6

3). 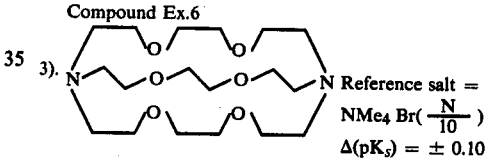 Reference salt = NMe$_4$ Br($\frac{N}{10}$)

$\Delta(pK_s) = \pm 0.10$

| Cation | $K_s$ | $-pK_s$ |
|---|---|---|
| Mg$^{++}$ | <10$^2$ | >2 |
| Ca$^{++}$ | 1.74×10$^4$ | 4.24 |
| Sr$^{++}$ | 1.02×10$^8$ | 8.01 |
| Ba$^{++}$ | 3.0×10$^9$ | 9.48 |

Compound Ex. 22

4). 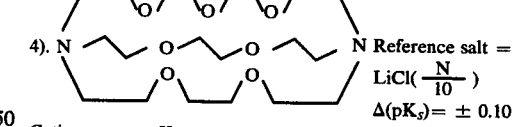 Reference salt = LiCl($\frac{N}{10}$)

$\Delta(pK_s) = \pm 0.10$

| Cation | $K_s$ | $-pK_s$ |
|---|---|---|
| Mg$^{++}$ } | <10$^2$ } | <2 |
| Ca$^{++}$ | | |
| Sr$^{++}$ | 2×10$^3$ | 3.30 |
| Ba$^{++}$ | 5.6×10$^5$ | 5.75 |

Compounds Ex. 24

5). 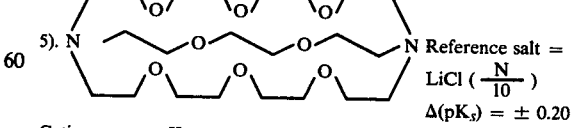 Reference salt = LiCl ($\frac{N}{10}$)

$\Delta(pK_s) = \pm 0.20$

| Cation | $K_s$ | $-pK_s$ |
|---|---|---|
| Mg$^{++}$ | | |
| Ca$^{++}$ } | <10$^2$ } | <2 |
| Sr$^{++}$ | | |
| Ba$^{++}$ | 3×10$^3$ | 3.48 |

Compound Ex. 18

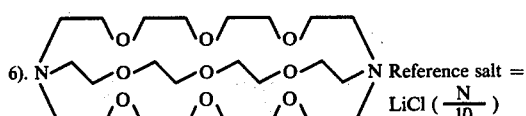

6). Reference salt = LiCl ($\frac{N}{10}$)

For Mg, Ca, Sr: $-pK_s < 2$
For $Ba^{++}$: $K_s = 5.1 \times 10^4$
$-pK_s = 4.71 \pm 0.20$

---

(C) Other cations studied
Compound Ex. 43

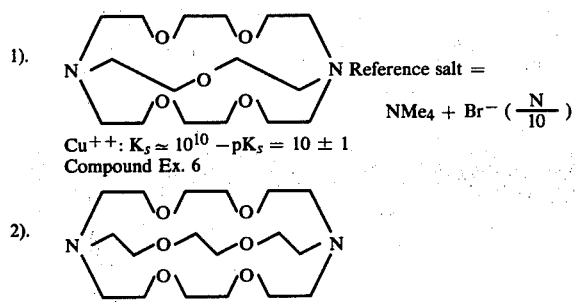

1). Reference salt = $NMe_4 + Br^- (\frac{N}{10})$ $Cu^{++}$: $K_s \simeq 10^{10}$ $-pK_s = 10 \pm 1$
Compound Ex. 6

2).

| Cation | $K_s$ | $-pK_s$ | $\Delta pK_s$ | Reference Salt |
|---|---|---|---|---|
| $Ag^+$ | $4.1 \times 10^9$ | 9.61 | $\pm 0.20$ | Without reference salt |
| $Tl^+$ | $2.1 \times 10^6$ | 6.32 | $\pm 0.20$ | Without reference salt |
| $Pb^{++}$ | $1.13 \times 10^{12}$ | 12.05 | $\pm 0.10$ | $NMe_4Br (\frac{N}{10})$ |

Compound Ex. 22

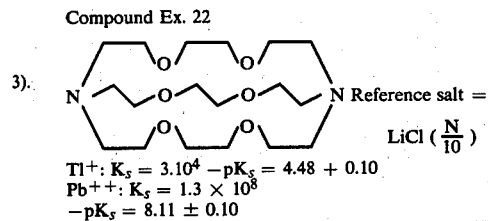

3). Reference salt = LiCl ($\frac{N}{10}$)

$Tl^+$: $K_s = 3.10^4$ $-pK_s = 4.48 + 0.10$
$Pb^{++}$: $K_s = 1.3 \times 10^8$
$-pK_s = 8.11 \pm 0.10$

---

The following examples further illustrate the practice of this invention. My invention is not to be construed as limited to the specific embodiments described therein but, rather, to include modifications thereof obvious to those skilled in the art.

EXAMPLE 1

Preparation of Triglycolyl Chloride

A. Preparation of Triglycolic Acid 100 g. of nitric acid (density = 1.38) are heated to 45° C. 20 g. of triethylene glycol are added in small portions so as to keep the temperature at about 45° C. to 50° C. After this step the mixture is agitated for about 20 minutes at 45° C. and then for one hour at about 80° C. The solution is evaporated under vacuum at 70° C. for 2 to 3 hours. A viscous paste of a brownish colour is obtained. 100–120 ml of benzene are added and water is distilled off. Upon cooling, the diacid crystallizes and is recrystallized from a mixture of acetone and benzene. The solid is dried under a vacuum of 0.1 mm. Hg and the acid obtained has m.p. = 74° C.–75° C.

PMR (in $D_2O$): 3.80 ppm (singlet), 4.25 ppm (singlet)

B. Preparation of Triglycolyl Chloride 15 g. of the acid obtained above, 30 g. of oxalyl chloride, 100 ml. anhydrous benzene and three drops of pyridine are mixed and agitated for 24 hours. Petroleum ether is added and the product is decanted. The mixture is filtered and the benzene and the excess of oxalyl chloride is evaporated on a rotatory evaporator without heating. The evaporation is repeated twice, each time with 100 ml. of benzene. The product obtained is a yellow oil. The oil is diluted with a mixture of ethyl ether and petroleum ether and after cooling to a temperature between room temperature and −70° C., the product crystallizes out. The crystals are then washed with petroleum ether, care being taken that the product does not come into contact with moisture in the air. After recrystallizing twice and washing twice with ether, the product is dried under a vacuum of 0.1 mm. Hg. m.p. = 20° C.–30° C. (crude product).

PMR ($CDCl_3$): 3.85 ppm (singlet); 4.52 ppm (singlet).

EXAMPLE 2

Preparation of 1,8-Diamino-3,6-dioxaoctane

A. Preparation of Triethylene Clycol Dibromide 66 g. of triethylene glycol and 13.3 g. of anhydrous pyridine are slowly added to 100 g. of phosphorous tribromide while agitating and cooling the mixture. After standing overnight at room temperature, the mixture is poured on to ice and the organic phase is decanted, washed with water and dilute hydrochloric acid and dried over sodium sulphate. After distillation under vacuum (95° C. and 0.5 mm. Hg) the title compound is obtained.

Yield: 60–70%

PMR ($CDCl_3$): 3.4–4.0 ppm (multiplet); 3.70 ppm (singlet)

B. Preparation of Triethylene Glycol Diphtalimide 161 g. of phtalimide are mixed with 50 g. of potassium hydroxide in 500 ml. ethanol. The mixture is agitated for 24 hours and filtered and potassium phthalimide is obtained. 7.5 g. of the dibromide obtained in part A of this example is mixed with 30 ml. dimethylformamide and 9 g. of the potassium phthalimide obtained above, and the mixture is heated for one hour at 100° C. After cooling, 50 ml. water and 50 ml. chloroform are added. After decantation, the organic layer is washed with dilute potassium hydroxide, then with water and is dried over potassium sulphate and evaporated. The title compound crystallizes out and is recrystallized from acetic acid.

Yield 95%.

m.p.: 175° C.

PMR ($CDCl_3$): 3.5–3.85 ppm (multiplet); 3.60 ppm (singlet); 7.80 (multiplet).

C. Preparation of 1,8-Diamino-3,6-dioxaoctane 22.4 g. of the product obtained in step B are suspended in 250 ml. ethanol and heated under reflux. 19 ml. of $N_2H_4$ and water (50%) are added and the heating under reflux is continued for 2 hours. After this time, the reaction is practically finished. 25 ml. of 10N hydrochloric acid is added and the mixture is heated under reflux for an additional half hour. The majority of the alcohol is distilled off, and the residual solution is filtered and saturated with potassium hydroxide. The mixture is poured into a liquid-liquid extractor and extracted with benzene. The benzene solution is evaporated, and the diamine distilled under a vacuum of 0.5 mm. Hg at 88° C.

Yield = 70%.

PMR ($CDCl_3$): $CH_2$—N: 2.85 ppm (triplet); $CH_2$—O: 3.50 ppm (triplet) and 3.60 ppm (singlet).

EXAMPLE 3 cl Preparation of 5,12-Dioxo-1,7,10,16-tetraoxa-4,13-diazacyclooctadecane

This reaction is carried out applying a high dilution technique. A solution of 14.8 g of the diamine obtained in Example 2 (0.1 mole) in 500 ml. anhydrous benzene and a solution of 11.2 g. of the dichloride obtained in Example 1 in 500 ml. anhydrous benzene are added to 1,200 ml. anhydrous benzene over a period of 8 hours under vigorous agitation and under a nitrogen atmosphere. On termination, the benzne solution is filtered and evaporated to dryness. The crystalline residue is dissolved in anhydrous benzene and passed through a column of aluminum oxide. The polymers formed during the reaction are retained and a pure solution of the desired compound is obtained. After recrystallization from a mixture of benzene and heptane, the title product is produced.

m.p. = 111° C.
Yield = 70%.
PMR (CDCl$_3$): —CO—CH$_2$—O: 4.00 ppm (singlet); —CH$_2$—N and —CH$_2$—O: 3.6ppm (multiplet)

EXAMPLE 4

Preparation of 1,7,10,16-Tetraoxa-4,13-diazacyclooctadecane

A solution of 18.5 g. of the diamide obtained in Example 3 in 450 ml. anhydrous tetrahydrofurane is slowly added to a mixture of 150 ml. anhydrous tetrahydrofurane and 12 g. LiAlH$_4$ while stirring and heating at the reflux temperature. After the addition is completed, the mixture is stirred under reflux and under a nitrogen atmosphere for 24 hours. After cooling to room temperature the excess reagent is destroyed by adding a mixture of water and THF (1:2). The mixture is filtered and the filtrate is evaporated to dryness. The residue is dissolved in benzene and the solution is passed through a column of Al$_2$O$_3$ with benzene as eluant. The solution is evaporated to dryness and after recrystallization from benzene/petrol ether 13.5 g. of the desired product is obtained.

m.p. = 115° C.-116° C.
Yield: 80%.
PMR (CDCl$_3$). —CH$_2$—O: 3.58 ppm (singlet + triplet); —CH$_2$—N: 2.78 ppm (triplet)

EXAMPLE 5

Preparation of 2,9-Dioxo-4,7,13,16,21,24-hexaoxa-1,10-diazabicyclo[8,8,8]hexacosane The reaction is carried out applying the high dilution technique.

A solution of 5.24 g. of the cyclic diamine obtained in Example 4 and 4.4 g. of triethylamine in 500 ml. anhydrous benzene and a solution of the dichloride (4.4 g. in 500 ml. anhydrous benzene) obtained in Example 1B is added to 1000 ml. anhydrous benzene during 10 hours under nitrogen atmosphere and under agitation. The salt of triethylamine and the hydrochloric acid precipitates and is filtered off. The filtrate is evaporated to dryness. The residue is dissolved in benzene and passed through a column of Al$_2$O$_3$ using benzene as an eluant. The product is crystallized from a hexane-benzene mixture.

m.p. = 114° C.
Yield 50%.

PMR (CDCl$_3$): several peaks between 3.3 and 4.6 ppm

EXAMPLE 6

Preparation of 4,7,13,16,21,24-hexaoxa-1,10-diazabicyclo[8,8,8]-hexacosane

B$_2$H$_6$ is prepared according to the process described in "Org. Reactions" 13, 3132 (1963). A solution of 1 g. of the bicyclo diamide obtained in Example 5 in 20 ml. tetrahydrofurane is slowly added to 15 ml. of the fresh prepared B$_2$H$_6$ solution under nitrogen atmosphere and at a temperature of 0° C. The mixture is agitated at this temperature for 30 minutes and thereafter 1 hour at reflux temperature. The excess reagent is destroyed by adding 5 ml. of water and the solution is evaporated on a rotatory evaporator under vacuum. 1 g. of the diborane of the title compound is obtained:

$$BH_3 - \overset{+}{N} \underset{\underset{O}{\diagdown}\diagup}{\overset{\diagup O \diagdown \diagup O \diagdown}{\diagup\underset{O}{\diagdown}\diagup}} \overset{+}{N} - BH_3$$

This compound is hydrolysed by adding 20 ml. 6N hydrochloric acid under heating and a solution is obtained. The mixture is evaporated to dryness under vacuum on a rotatory evaporator. The residue is dissolved in 10 ml. water and the solution is passed through a column of an anion exchange resin (Dowex 1). The column is washed with water until there is no basic reaction. The water is evaporated. The residue is recrystallized from hexane and dried in vacuum (0.1 mm. Hg.) 890 mg. of the desired product is obtained.

m.p. 68° C.-69° C.
Yield 95%.
PMR (CDCl$_3$): —CH$_2$N: 2.65 ppm (triplet); —CH$_2$—O: 3.65 ppm (singlet + triplet)

EXAMPLE 7

Preparation of 4,13-Dimethyoxycarbonyl-1,7,10,16-tetraoxa-4,13-diazacyclooctadecane 3.6 g of the diamine obtained in Example 4 are dissolved in 30 ml. methanol and 3 ml. water. A solution of 3.6 g. ClCO$_2$CH$_3$ in 15 ml. methanol is added while cooling and agitating. The agitation is maintained for 24 hours. The mixture is filtered and the filtrate evaporated to dryness. The residue is recrystallized from CHCl$_3$/petroleum ether.

m.p. = 104° C.
Yield 80%
PMR (CDCl$_3$): Signals at about 3.65 ppm.

EXAMPLE 8

Preparation of 4,13-Dimethyl-1,7,10,16-tetraoxa-4,13-diazacyclooctadecane

A: 3 g. of the compound of Example 7 dissolved in 20 ml. dry ether are slowly added to 3 g. LiAlH$_4$ in 5 ml. dry ether. The mixture is agitated for 24 hours. Then 3 g. KOH in 6 ml. H$_2$O is added followed by 10 ml. H$_2$O. The mixture is filtered and evaporated to dryness. The residue is extracted with ether and benzene. The solution is evaporated to dryness and an oil which boils at 97° C. by a pressure of 0.05 mm. Hg is obtained.

PMR (CDCl$_3$): —CH$_2$-N: 2.70 ppm (triplet); N—CH$_3$ 2.32 ppm (singlet); —CH$_2$—O: 3.65 ppm (singlet + triplet)

B. Alternatively this compound may be obtained by reacting N,N'-dimethyl-1,8-diamino-3,6-dioxaoctane with triglycolyle chloride following the procedure of Examples 3 and 4.

EXAMPLE 9

Preparation of the KSCN-Complex of 1,7,10,16-Tetraoxa-4,13-diaza-cyclooctadecane 524 mg. of the macrocyclic compound obtained in Example 4 and 194 mg. of KSCN are refluxed in 20 ml. of acetone for 5 minutes. The acetone is then removed under vacuum, and the residue is recrystallized from CHCl$_3$/Petroleum ether. The crystalline complex melts at 167° C.–168° C.

EXAMPLE 10

Preparation of the CuCl$_2$-Complex of 1,7,10,16-Tetraoxa-4,13-diaza-cyclooctadecane A solution of 2.62 g. of the macrocyclic compound obtained in Example 4 in 10 ml. CH$_3$OH is mixed with a solution of 1.70 g. of CuCl$_2$.2H$_2$O in 10 ml. CH$_3$OH. The blue complex is immediately formed and precipitates. After filtration and recrystallization from CHCl$_3$/CH$_3$OH the pure complex is obtained.

EXAMPLE 11

Preparation of the RbSCN-Complex of 4,7,13,16,21,24-hexaoxa-1,10-diazabicyclo[8,8,8]hexacosane 130 mg. amine macrocyclic obtained in Example 6 and 35 mg. RbSCN are mixed in a flask. 20 ml. acetone are added. The mixture is heated to the boiling point until all solid material has dissolved. After evaporation to dryness the residue is extracted with chloroform, which dissolves the complex. The chloroform solution is also evaporated to dryness, yielding the crystalline complex. The complex may be recrystallized from acetone-heptane. It melts at 163° C.–164° C.

PMR (CDCl$_3$): —CH$_2$—N: 2.56 ppm (triplet)

EXAMPLE 12

Preparation of the BaCl$_2$-Complex of 4,7,13,16,21,24-hexaoxa-1,10-diazabicyclo[8,8,8]hexacosane 37.6 mg. amine macrocylic obtained in Example 6 and 21 mg. BaCl$_2$, 2H$_2$O are dissolved in 10 ml. water. The solution is then evaporated to dryness. The solid residue is extracted with methylene chloride. After filtration of the solution, ether is added until crystallization sets in. The crystalline complex does not melt but darkens at about 200° C.

PMR (CDCl$_3$): —CH$_2$—N: 2.80 ppm (triplet)

EXAMPLE 13

Preparation of Tetraglycolyl Chloride

A: Preparation of Tetraglycolic Acid 100 g. of nitric acid (density = 1.38) are heated to 45° C. 20 g. of tetraethylene glycol are added in small portions so as to keep the temperature at about 45° C.–50° C. After this step the mixture is agitated for about 20 minutes at 45° C. and then for one hour about 80° C. The solution is evaporated under vacuum at 70° C. for 2 to 3 hours. A viscous paste of a brownish colour is obtained. 100 to 120 ml. of benzene are added and water is distilled off. The diacid is a viscous oil which does not crystallize.

PMR (D$_2$O): 3.75 ppm (singlet); 4.22 ppm (singlet)

B: Preparation of Tetraglycolyl Chloride 28 g. of the acid obtained above, 50 g. of oxalyl chloride, 200 ml. anhydrous benzene and six drops of pyridine are mixed and agitated for 6 hours. The mixture is filtered and the benzene and the excess of oxalyl chloride is evaporated on a rotatory evaporator without heating. The evaporation is repeated twice, each time with 100 ml. of benzene. The product obtained is a yellow oil, which does not crystallize.

PMR (CDCl$_3$): 3.75 ppm (multiplet); 4.52 ppm (singlet)

EXAMPLE 14

Preparation of 1,11-Diamino-3,6,9-trioxaundecane

A: Preparation of Tetraethylene Glycol Dibromide 300 g. of tetraethylene glycol and 100 g. of anhydrous pyridine are slowly added to 727 g. of phosphorus tribromide, while agitating and cooling the mixture. After cooling to room temperature, the mixture is poured on to ice and the organic phase is decanted, washed with water and dilute hydrochloric acid and dried over sodium sulphate. After distillation under vacuum (123° C.–125° C. and 0.4 mm. Hg) the title comound is obtained.

Yield: 60%.

PMR (CDCl$_3$): 3.70 ppm (multiplet)

B: Preparation of Tetraethylene Glycol Diphtalimide 161 g. of diphtalimide are mixed with 50 g. of potassium hydroxyde in 500 ml. ethanol. The mixture is agitated for 24 hours and filtered and potassium phtalimide is obtained. 217 g. of the dibromide obtained in part A of this example is mixed with 1000 ml. dimethylformamide and 260 g. of the potassium phtalimide obtained above, and the mixture is heated for eight hours at 100° C. After cooling, the mixture is poured into 3 liter cold water. The precipitate is filtered, washed with water and acetone and dried under vacuum. The title compound is recrystallized from ethanol.

Yield 85%, m.p. 108° C.–109° C.

PMR (CDCl$_3$): 3.60 ppm (singlet); 3.80 ppm (multiplet); 7.80 (multiplet)

C: Preparation of 1,11-Diamino-3,6,9-trioxaundecane 254 g. of the product obtained in step B are suspended in 1000 ml. ethanol and heated under reflux. 90 g. of N$_2$H$_4$ in 90 g. water is added and the heating under reflux is continued for 3 hours. After this time, the reaction is practically finished. 10N hydrochloric acid is added until pH 1 is obtained and the mixture is heated under reflux for an additional half hour. The residual mixture is filtered; the solution is evaporated to dryness. 250 ml. water are added and the solution is saturated with potassium hydroxide. The mixture is again filtered to remove precipitated KCl and is poured into a liquid-liquid extractor and extracted with benzene. The benzene solution is evaporated, and the diamine distilled under a vacuum of 0.2 mm Hg at 114° C.–116° C.

Yield = 72%.

PMR (CDCl$_3$): —NH$_2$: 1.30 ppm (singlet); CH$_2$—N: 2.85 ppm (triplet); —CH$_2$—O: 3.48 ppm (triplet) and 3.60 ppm (singlet).

EXAMPLE 15

Preparation of 5,15-Dioxo-1,7,10,13,19,22-hexaoxa-4,16-diaza-cyclotetracosane

This reaction is carried out applying a high dilution technique. A solution of 15.4 g. of the diamine obtained in Example 14 in 500 ml. anhydrous benzene and a solution of 10.4 g. of the dichloride obtained in Example 13 in 500 ml. anhydrous benzene are added to 1,200 ml. anhydrous benzene over a period of 10 hours under vigorous agitation and under a nitrogen atmosphere. On termination, the benzene solution is filtered and evaporated to dryness. The oily residue is dissolved in anhydrous benzene and passed through a column of aluminium oxide. The polymers formed during the reaction are retained and a pure solution of the desired compound is obtained. After evaporation of the benzene, the title product is produced as a viscous oil.

Yield = 68%.

PMR (CDCl$_3$): —CH$_2$—O and —CH$_2$—N: 3.60 ppm (three peaks) —CO—CH$_2$—O: 3.85 ppm (singlet)

EXAMPLE 16

Preparation of 1,7,10,13,19,22-Hexaoxa-4,16-diazacyclotetracosane

A solution of 30 g. of the diamide obtained in Example 15 in 200 ml. anhydrous tetrahydrofurane is slowly added to a mixture of 50 ml. anhydrous tetrahyfrofurane and 18 g. LiAlH$_4$ while stirring and heating at the reflux temperature. After the addition is completed, the mixture is stirred under reflux and under a nitrogen atmosphere for 24 hours. After cooling to room temperature the reducing agent is destroyed by adding a mixture of water and THF (1:2). The mixture is filtered and the filtrate is evaporated to dryness. The residue is dissolved in benzene and the solution is passed through a column of Al$_2$O$_3$ with benzene as eluant. The solution is evaporated to dryness and the desired product is obtained as a colourless oil which crystallizes at low temperatures.

m.p. = 15° C.

Yield 95%.

PMR (CDCl$_3$): NH: 2.10 ppm (singlet); CH$_2$—N: 2.80 ppm (triplet); CH$_2$—O—: 3.60 ppm (singlet and triplet).

EXAMPLE 17

Preparation of 2,12-dioxo-4,7,10,16,19,22,27,30,33-nonaoxa-1,13-diazabicyclo[11,11,11]pentatriacontane The reaction is carried out applying the high dilution technique. A solution of 7.0 g. of the cyclic diamine obtained in Example 16 and 4.4 g. of triethylamine in 500 ml. anhydrous benzene and a solution of the dichloride (5.2 g. in 500 ml. anhydrous benzene) obtained in Example 13B is added to 1200 ml anhydrous benzene during ten hours under nitrogen atmosphere and under agitation. The salt of triethylamine and the hydrochloric acid precipitates and is filtered off. The filtrate is evaporated to dryness. The residue is dissolved in benzene and passed through a column of Al$_2$O$_3$ using benzene as an eluant. The product is a colourless oil which crystallizes on standing.

m.p. 72°-74° C.

Yield = 65%

PMR (CDCl$_3$): 3.4–3.8 ppm (broad peaks); —CO—CH$_2$—N: 4.33 ppm (broad peak).

EXAMPLE 18

Preparation of 4,7,10,16,19,22,27,30,33-nonaoxa-1,13-diaza-bicyclo[11,11,11]pentatriacontane B$_2$H$_6$ is prepared according to the process described in "Org. Reactions" 13, 31–32 (1963).

A solution of 1.3 g. of the bicyclic diamide obtained in Example 17 in 20 ml. tetrahydrofurane is slowly added to 15 ml. of the fresh prepared B$_2$H$_6$ solution (1.6 mole) under nitrogen atmosphere and at a temperature of 0° C. The mixture is agitated at this temperature for 30 minutes and thereafter 2 hours at reflux temperature. After cooling to room temperature the excess reagent is destroyed by adding 10 ml. of water and the solution is evaporated on a rotatory evaporator under vacuum. The bis-amine-borane of the title compound is obtained by extraction of the residue with chloroform.

This compound is hydrolysed by adding 25 ml. 6N hydrochloric acid under heating to reflux for 3 hours and a solution is obtained. The mixture is evaporated under vacuum on a rotatory evaporator. The residue is dissolved in 10 ml. water and the solution is passed through a column of an anion exchange resin (Dowex 1). The column is washed with water until there is no basic reaction. The water is evaporated. The residue is the desired product, obtained as a colourless oil.

Yield 95%.

PMR (CDCl$_3$): —CH$_2$—N: 2.85 ppm (triplet); —CH$_2$—O: 3.65 ppm (singlet and triplet)

EXAMPLE 19

Preparation of 5,12-Dioxo-1,7,10,16,19-pentaoxa-4,13-diaza-cycloheneicosane

This reaction is carried out applying a high dilution technique. A solution of 31.8 g. of the diamine obtained in Example 14 in 1000 ml. anhydrous benzene and a solution of 17.8 g. of the dichloride obtained in Example 1 in 1000 ml. anhydrous benzene are added to 1,200 ml. anhydrous benzene over a period of 14 hours under vigorous agitation and under a nitrogen atmosphere. On termination, the benzene solution is filtered and evaporated to dryness. The crystalline residue (25 g.) is dissolved in anhydrous benzene and passed through a column of aluminium oxide. The polymers formed during the reaction are retained and a pure solution of the desired compound is obtained. After recrystallization from a mixture of benzene and heptane, the title product is produced.

m.p. = 90° C.-91° C.

Yield 75%.

PMR (CDCl$_3$): —CH$_2$—O— and —CH$_2$—N: 3.5 to 3.9 ppm (complex multiplet); —CO—CH$_2$—O: 4.05 ppm (singlet).

EXAMPLE 20

Preparation of 1,7,10,16,19-Pentaoxa-4,13-diazacycloheneicosane

A solution of 6.7 g. of the diamide obtained in Example 19 in 100 ml. anhydrous tetrahydrofurane is slowly added to a mixture of 50 ml. anhydrous tetrahydrofurane and 3.8 g. LiAlH$_4$ while stirring. After the addition is complete, the mixture is stirred under reflux and under a nitrogen atmosphere for 11 hours. After cooling to room temperature, the reagent is destroyed by adding 10 ml. water in 25 ml. THF, followed by 10 ml. NaOH (15% in water) and then 30 ml. water. The mixture is filtered and the filtrate is evaporated to dryness. The residue is dissolved in benzene and the solution is passed through a column of $Al_2O_3$ with benzene as eluant. The solution is evaporated to dryness and the desired product is obtained as a colourless oil which crystallizes at low temperature.

m.p. about 0° C.
Yield 70%.
PMR (CDCl$_3$): NH: 2.50 ppm (singlet); —CH$_2$—N: 2.80 ppm (triplet); —CH$_2$—O: 3.5–3.7 ppm (two singlets + triplet).

EXAMPLE 21

Preparation of 14,21,Dioxo-4,7,10,16,19,24,27-heptaoxa-1,13-diazabicyclo[8,8,11]nonacosane The reaction is carried out applying the high dilution technique. A solution of 2.55 g. of the cyclic diamine obtained in Example 20 and 2 g. of triethylamine in 200 ml. anhydrous benzene and a solution of the dichloride (1.8 g. in 200 ml. anhydrous benzene) obtained in Example 1B is added to 1200 ml. benzene during 5 hours under nitrogen atmosphere and under agitation. The salt of triethylamine and hydrochloric acid precipitates and is filtered off. The filtrate is evaporated to dryness. The residue is dissolved in benzene and passed through a column of $Al_2O_3$ using benzene as an eluant. After evaporation of the solvent, the residue crystallizes on standing. The product obtained is the desired compound.

m.p. = 97° C.–98° C.
Yield 65%.
PMR (CDCl$_3$): CH$_2$—N and CH$_2$—O: 3.5–3.9 ppm (broad peaks); CO—CH$_2$—O: 4.0–4.3 ppm (very broad peaks).

EXAMPLE 22

Preparation of 4,7,10,16,18,24,27-heptaoxa-1,13-diazabicyclo[8,8,11]nonacosane $B_2H_6$ is prepared according to the process described in "Org. Reactions", 13, 31–32 (1963).

A solution of 1.5 g. of the bicyclic diamide obtained in Example 21 in 15 ml. anhydrous tetrahydrofurane is slowly added to 15 ml. of the fresh prepared $B_2H_6$ solution (1.2 M) under nitrogen atmosphere and at a temperature of 0° C. The mixture is agitated at this temperature for 30 minutes and thereafter 2 hours at reflux temperature. The excess reagent is destroyed by adding 5 ml. of water and the solution is evaporated on a rotatory evaporator under vacuum. The bis-amineborane of the title compound is obtained.

This compound is hydrolysed by adding 30 ml. 6N hydrochloric acid under heating at reflux for 2 hours and a solution is obtained. The mixture is evaporated under vacuum on a rotatory evaporator. The residue is dissolved in 10 ml. water and the solution is passed through a column of an anion exchange resin (Dowex 1). The column is washed with water until there is no basic reaction. The water is evaporated. The residue is dried in vacuum (0.1 mm. Hg). 1 g of the desired product is obtained as a colourless liquid.

Yield 75%.

PMR (CDCl$_3$): —CH$_2$—N: 2.75 ppm (triplet); —CH$_2$—O. 3.70 ppm (singlet); 3.65 ppm (triplet).

EXAMPLE 23

Preparation of 2,12-Dioxo-4,7,10,16,19,22,27,30-octaoxa-1,13-diazabicyclo[8,11,11]dotriacontane The reaction is carried out applying the high dilution technique.

A solution of 1.67 g. of the cyclic diamine obtained in Example 20 and 1.2 g. of the triethylamine in 100 ml. anhydrous benzene and a solution of the dichloride (1.30 g. in 100 ml. anhydrous benzene) obtained in Example 13B is added to 1000 ml. benzene during 2 hours under nitrogen atmosphere and under agitation. The salt of triethylamine and the hydrochloric acid precipitates and is filtered off. The filtrate is evaporated to dryness. The residue is dissolved in benzene and passed through a column of $Al_2O_3$ using benzene as an eluent. The desired product is obtained as a colourless viscous oil.

Yield 50%.
PMR (CDCl$_3$): 3.45–3.8 ppm (broad peaks); —CO—CH$_2$—O: 4.35 pm (broad peak)

EXAMPLE 24

Preparation of 4,7,10,16,19,22,27,30-octaoxa-1,13-diazabicyclo[8,11,11]dotriacontane $B_2H_6$ is prepared according to the process described in "Org. Reactions" 13, 31–32 (1963).

A solution of 1.2 g. of the bicyclic diamide obtained in Example 23 in 20 ml. tetrahydrofurane is slowly added to 10 ml. of the fresh prepared $B_2H_6$ solution (1.6 M) under nitrogen atmosphere and at a temperature of 0° C. The mixture is agitated at this temperature for 30 minutes and thereafter 2 hours at reflux temperature. The excess reagent is destroyed by adding 3 ml. of water and the solution is evaporated on a rotatory evaporator under vacuum. 1.13 g. of bis-amineborane of the title compound is obtained by extracting the residue with chloroform.

This compound is hydrolysed by adding 40 ml. 6N hydrochloric acid under heating for 2 hours and a solution is obtained. The mixture is evaporated under vacuum on a rotatory evaporator. The residue is dissolved in 10 ml. water and the solution is passed through a column of an anion exchange resin (Dowex 1). The column is washed with water until there is no basic reaction. The water is evaporated. The residue is the desired product, obtained as a colourless liquid.

Yield 95%.
PMR (CDCl$_3$): —CH$_2$—N: 2.80 ppm (triplet); —CH$_2$—O—: 3.4–3.8 ppm (singlet and triplet)

EXAMPLE 25

Preparation of the CsSCN complex of 4,7,10,16,19,22,27,30,33-nonaoxa-1,13-diazabicyclo[11,11,11]pentatriacontana 100 mg. of the macrocyclic compound obtained in Example 18 and 45 mg. of CsSCN are refluxed in 20 ml. of acetone for 5 minutes. After filtration, the solvent is evaporated. The residue is extracted with chloroform, filtered again and evaporated to dryness. The complex is crystallized from acetone/ethyl acetate.

m.p. = 155° C.–156° C.

PMR (CDCl$_3$): —CH$_2$—N: 2.60 ppm (triplet); —CH$_2$—O: 3.55 ppm (triplet) and 3.62 ppm (singlet)

EXAMPLE 26

Preparation of Ethylene-bisthioglycolic acid dichloride

A. Preparation of Ethylene-bisthioglycolic acid

Thioglycolic acid (20 g.), water (20 ml.), ethanol (20 ml.), and a solution of sodium hydroxide (17.6 g.) in water (30 ml.) are mixed in a flask and heated at reflux temperature. 1,2-Dibromoethane (18.5 g.) is added with strong agitation over a period of three hours. The mixture is refluxed for another two hours. After filtration, the filtrate is evaporated to dryness and taken up in a mixture of water (100 ml.) and 12 N hydrochloric acid (60 ml.) The mixture is extracted with ether (50 ml. three times). The organic layer is separated, dried over sodium sulfate and evaporated to dryness to give the crystalline title compound which is then recrystallized from toluene.

m.p. = 107° C. (Yield 80%)

PMR (D$_2$O): S—CH$_2$—CH$_2$—S: 3.0 ppm (singlet; 4H): S—CH$_2$—CO: 3.55 ppm (singlet; 4H).

B. Preparation of the dichloride of the preceding acid 15 g. of the above diacid are added to a mixture of 100 ml. anhydrous benzene and 100 ml. anhydrous ether. Then 30 g. oxalyl chloride are added the flask being protected by a calcium chloride tube. The mixture is stirred for 36 hours and the diacid progressively dissolves as it is being transformed into the corresponding dichloride. The solution is then evaporated to dryness (without heating) leaving a brownish solid residue which is recrystallized from a mixture of anhydrous ether and petroleum ether by cooling at −70° C. in a dry ice-acetone mixture.

The solid yellowish dichloride is obtained in a nearly quantitative yield.

m.p. = approx. 30° C. (crude product)

PMR (CDCl$_3$): S—CH$_2$—CH$_2$—S: 2.92 ppm (singlet; 4H): S—CH$_2$—CO: 3.55 ppm (singlet: 4H)

EXAMPLE 27

Preparation of 3,6-dithia-1,8-diamino-octane 8.5 g. potassium metal are dissolved in 100 ml. anhydrous tertio-butanol (heating at 60° C. accelerates the process). When the metal is entirely dissolved 15.4 g. cysteamine are added at once. The mixture is stirred for one hour until all the solid has dissolved. 18.8 g. 1,2-dibromoethane are then added slowly (over approx. thirty minutes); the reaction is exothermic. The mixture is stirred overnight at room temperature, then filtered through a sintered glass funnel; the solid residue is washed with benzene. The combined organic layers are evaporated to dryness. A viscous brownish oil is obtained. This oil is taken up into benzene (100 ml.) and filtered through a short column of alumina (approx. 20 g.) The column is washed with an additional 250 ml. of benzene. The benzene solutions are evaporated to dryness. The yellowish residue crystallizes.

m.p. = approx. 35° C.-40° C. (Yield: 85)

PMR (CDCl$_3$): —NH$_2$: 1.32 ppm (singlet: 4H): S—CH$_2$—CH$_2$—S: 2.72 ppm (singlet: 4H): N—CH$_2$—CH$_2$—S: 2.75 ppm (multiplet: 8H)

EXAMPLE 28

Preparation of 3,14-Dioxo-1,16-dioxa-7,10-dithia-4,13-diaza-cyclooctadecane

This reaction is carried out applying a high dilution technique. A solution of 10.2 g. of the diamine obtained in Example 27 in 500 ml, anhydrous benzene and a solution of 6.1 g. of the dichloride obtained in Example 1B in 500 ml. anhydrous benzene are added to 1,200 ml. anhydrous benzene over a period of ten hours under vigorous agitation and under a nitrogen atmosphere. On termination, the benzene solution is filtered, the residue is washed with benzene and the combined benzene solutions are evaporated to dryness. The residue is dissolved in anhydrous benzene and passed through a short column of alumina (30 g.) The polymers formed during the reaction are retained and a pure solution of the desired compound is obtained. After recrystallization from a mixture of benzene and heptane, the title product is produced.

m.p. = 145° C.
Yield = 60%.

PMR (CDCl$_3$): S—CH$_2$-CH$_2$—S: 2.80 ppm (singlet: 4H): S—CH$_2$—: 2.80 ppm (multiplet: 4H); N—CH$_2$: 3.45 ppm (multiplet: 4H); O—CH$_2$—CH$_2$—O: 3.72 ppm (singlet: 4H); O—CH$_2$—CO: 4.0 ppm (singlet: 4H)

EXAMPLE 29

Preparation of 1,16-dioxa-7,10-dithia-4,13-diaza cyclooctadecane

A solution of 7 g. of the cyclic diamide obtained in Example 28 in 100 ml. anhydrous tetrahydrofurane is added slowly to 50 ml. of a freshly prepared solution (1.5 M) of diborane in anhydrous tetrahydrofuran under nitrogen atmosphere and at a temperature of 0° C. The mixture is then heated to reflux for two hours. The excess reagent is destroyed by adding 10 ml. of water and the solution is evaporated to dryness on a rotatory evaporator under vacuum. 100 ml. 6N hydrochloric acid are added to the residue and the mixture is refluxed for two hours; a clear solution is obtained. This solution is then evaporated to dryness under vacuum. The residue is dissolved in 30 ml. water and the solution is pressed through a column of an anion exchange resin (Dowex 1, Trade Mark). The column is washed with water until there is no basic reaction. The combined water solutions obtained are evaporated to dryness under vacuum on a water bath (80° C.-100° C.). The residue is recrystallized.

Yield = 70%.
m.p. − 45° C.

PMR (CDCl$_3$): CH$_2$—N+CH$_2$—S: 2.77 ppm (complex band: 16H): CH$_2$—O: 3.59 ppm (singlet: 4H; triplet: 4H)

EXAMPLE 30

Preparation of 2,9-Dioxo-4,7,13,16-tetraoxa-21,24-dithia-1,10-diazabicyclo[8,8,8]hexacosane The reaction is carried out applying the high dilution technique. A solution of 3.5 g. of the cyclic diamine obtained in Example 29 and 1.3 g. of triethylamine in 400 ml. anhydrous benzene and a solution of the dichloride (2.7 g. in 400 ml. anhydrous benzene) obtained in Example 1B are added to 1000 ml. benzene during eight hours under nitrogen atmosphere and under agitation. The triethylamine hydrochloride precipitates and is filtered off. The filtrate is evaporated to dryness. The residue is dissolved in benzene and passed through a column of $Al_2O_3$ (20 g.) using benzene as an eluant. The solutions are evaporated to dryness. The product is a viscous oil.

Yield 50%

PMR: —$CH_2$—S—$CH_2$—$CH_2$—S—$CH_2$: 2.8 ppm (complex broad band: 8H); $CH_2$—O+CO—N—$CH_2$: 3.6 ppm (broad signals: 20H); CO—$CH_2$—O—: 4.0 ppm (broad signals: 4H).

EXAMPLE 31

Preparation of 4,7,13,16-tetraoxa-21,24-dithia-1,10-diazabicyclo[8,8,8-]hexacosane A solution of 1.6 g. of the bicyclic diamide obtained in Example 30 in 30 ml. anhydrous tetrahydrofuran is slowly added to 20 ml. of the fresh prepared diborane solution (1.5 N) under nitrogen atmosphere and a temperature of 0° C. The mixture is stirred two hours at reflux temperature. The excess reagent is destroyed by adding 5 ml. of water and the solution is evaporated on a rotary evaporator under vacuum. This residue is treated with 50 ml. 6 N hydrochloric acid under heating at reflux for two hours and a solution is obtained. The mixture is evaporated under vacuum on a rotary evaporator (water bath 80°-100° C.). The residue is dissolved in 50 ml. water and the solution is passed through a column of an anion exchange resin (Dowex 1, Trade Mark). The column is washed with water until there is no basic reaction. The water is evaporated. The residue is dried in vacuum (0.1 mm. Hg) and recrystallized from a benzene and heptane mixture, yielding the desired compound.

m.p. = 78° C.-80° C. (Yield: 95%)

PMR ($CDCl_3$): N—$CH_2$—$CH_2$—S+N—$CH_2$: 2.65 ppm (multiplet: 16H); S—$CH_2$—$CH_2$—S: 2.90 ppm (singlet: 4H), O—$CH_2$—: 3.60 ppm (triplet: 8H); 3.65 ppm (singlet: 8H)

EXAMPLE 32

Preparation of 5,12-dioxo-1,7,10,16-tetrathia-4,13-diaza-cyclooctadecane

This reaction is carried out applying a high dilution technique. A solution of 18 g. of the diamine obtained in Example 27 (0.1 mole) in 500 ml. anhydrous benzene and a solution of 12.4 g. of the dichloride obtained in Example 26 in 500 ml. anhydrous benzene are added to 1,200 ml. anhydrous benzene over a period of eight hours under vigorous agitation and under a nitrogen atmosphere. Most of the desired amide precipitates during the course of the reaction. On termination, the benzene solution is filtered and evaporated to dryness. A small amount (2g.) of solid residue is obtained. The solid precipitates formed during the high dilution reaction are extracted three times with 250 ml. boiling chloroform. The residue obtained from the benzene layer is added to the combined chloroform extracts. This solution is then filtered through a short column of alumina (30 g.), the column being washed with an additional 1,000 ml. of chloroform. The solution obtained is concentrated and the desired diamide crystallizes out.

m.p. = 148° C.-149° C.
Yield = 85%.

PMR ($CDCl_3$): —$CH_2$—S—: 2.65-2.90 ppm (complex band: 12H); —CO—$CH_2$—S: 3.25 ppm (singlet: 4H); —N—$CH_2$—: 3.52 ppm (multiplet: 4H)

EXAMPLE 33

Preparation of 1,7,10,16-tetrathia-4,13-diazacyclooctadecane

A solution of diborane (20 ml.; 1.5 N) in anhydrous tetrahydrofuran is added dropwise to a suspension of 2 g. of the diamide obtained in Example 32 in 50 ml. anhydrous tetrahydrofurane under nitrogen at room temperature. The solid dissolves giving a clear solution. After the addition is completed the mixture is refluxed during four hours and a solid precipitate is formed. After cooling to room temperature, the excess reagent is destroyed by adding carefully 10 ml. of water. The solvents are evaporated to dryness and 6 N hydrochloric acid (50 ml.) is added to the solid residue. The mixture is refluxed for three hours: the solid does not dissolve, the mixture remaining heterogeneous. The mixture is evaporated to dryness and a solution of 10% sodium hydroxide in water (50 ml.) is added to the residue.

The heterogeneous mixture is extracted three times with chloroform (50 ml.) The combined chloroform layers are dried over sodium sulfate and filtered through a short alumina (20 g.) column. The solvent is removed and the solid product is recrystallized from ethanol.

m.p. = 125° C.
Yield 50%.

PMR ($CDCl_3$): one complex band from 2.75 to 2.83 ppm.

EXAMPLE 34

Preparation of 2,9-dioxo-4,7-dioxa-13,16,21,24-tetrathia-1,10-diazabicyclo[8,8,8]-hexacosane The reaction is carried out applying the high dilution technique. A solution of 1.0 g. of the cyclic diamine obtained in Example 33 and 0.3 g. of triethylamine in 100 ml. anhydrous benzene and a solution of the dichloride (0.8 g. in 100 ml. anhydrous benzene) obtained in Example 1B are added to 1,000 ml. anhydrous benzene during two hours under nitrogen atmosphere and under vigorous agitation. The salt of triethylamine and the hydrochloric acid precipitates and is filtered off. The filtrate is evaporated to dryness. The residue is dissolved in benzene and filtered through a column of $Al_2O_3$ (20 g.) followed by 500 ml. of chloroform.

The solvents are evapoated, leaving the title compound as a viscous oil which may crystallize on standing.

Yield: 40%

PMR ($CDCl_3$): $CH_2$—S: 2.75 ppm (broad band: 16H); $CH_2$—N and $CH_2$—O: 3.65 ppm (broad bands: singlet + triplet: 12H); CO—$CH_2$—O: around 4 ppm (several broad peaks: 4H)

EXAMPLE 35

Preparation of 4,7-dioxa-13,16,21,24-tetrathia-1,10-diazabicyclo[8,8,8-]hexacosane A solution of 0.6 g. of the bicyclic diamide obtained in Example 34 in 10 ml. tetrahydrofuran is slowly added to 10 ml. of the freshly prepared $B_2H_6$ solution (1.5 M) under nitrogen atmosphere and at a temperature of 0° C.

The mixture is refluxed for two hours. The excess reagent is destroyed by adding 5 ml. of water and the solution is evaporated on a rotatory evaporator under vacuum. The solid residue is treated with 50 ml. 6 N hydrochloric acid under reflux for two hours. The mixture is evaporated to dryness under vacuum on a rotatory evaporator. The residue is treated with a solution of tetraethylammonium hydroxide until a basic reaction is obtained. The mixture containing a precpitate, is extracted several times with chloroform. The solutions are filtered through alumina and evaporated to dryness leaving the title compound as a crystalline residue.

The solid residue is recrystallized from a benzene-hexane mixture and dried in vacuum (0.1 mm Hg.)
m.p. = 86° C.-87° C.
Yield = 95%).
PMR (CDCl$_3$): N—CH$_2$—CH$_2$—S+N—CH$_2$: 2.70 ppm (multiplet: 20H); S—CH$_2$—CH$_2$—S: 2.90 ppm (broad band: 8H); CH$_2$—O: 3.60 ppm (triplet: 4H): 3.68 ppm (singlet: 4H).

EXAMPLE 36

Preparation of 2,9-dioxo-4,7,13,16,21,24-hexathia-1,10-diazabicyclo[8,8,8]hexacosane The reaction is carried out applying the high dilution technique. A solution of 4.5 g. of the cyclic diamine obtained in Example 33 and 1.5 g. of triethylamine in 500 ml. hot anhydrous benzene (maintained at approx. 60° C. during the addition) or in 400 ml. anhydrous chloroform and a solution of the dichloride (3.5 g. in 400 ml. anhydrous benzene) obtained in Example 26B is added to 1000 ml. anhydrous benzene during six hours under nitrogen atmosphere and under vigorous agitation. The salt of triethylamine and the hydrochloric acid and the product precipitate and are filtered off. The benzene layer contains only a very small amount of product. The solid is extracted three times with hot chloroform. The combined chloroform solutions are filtered through an alumina column. The bicyclic amide is eluted with methanol. After evaporation to dryness the title product is obtained as a viscous oil.
Yield 20%
PMR (CDCl$_3$): CH$_2$—S: several broad peaks between 2.5 and 3.1 ppm (20H); COCH$_2$—S+CH$_2$—N: several broad peaks between 3.2 and 3.8 ppm (12H).

EXAMPLE 37

Preparation of 4,7,13,16,21,24-hexathial,10-diazabicyclo[8,8,8]hexacosane 20 ml. of the fresh prepared B$_2$H$_6$ solution is added to a suspension of 1 g. of the bicyclic diamide obtained in Example 36 in 20 ml. tetrahydrofuran under nitrogen atmosphere and at a temperature of 0° C. The mixture is agitated at this temperature for thirty minutes and thereafter four hours at reflux temperature. The excess reagent is destroyed by adding 5 ml. of water and the solution is evaporated on a rotatory evaporator under vacuum. 50 ml. 6 N hydrochloric acid are added and the mixture is heated under reflux for four hours. The mixture is evaporated to dryness under vacuum on a rotatory evaporator. The mixture is made alkaline with NaOH N/10 and is extracted three times with chloroform. The chloroform solutions are filtered through alumina and evaporated to dryness. The residue is recrystallized from a chloroform/hexane mixture loading to the title compound.
m.p. = 172° C.
Yield = 80%.
PMR (CDCl$_3$): N—CH$_2$—CH$_2$—S: 2.68 ppm (singlet: 24H): S—CH$_2$—CH$_2$—S: 2.90 ppm (singlet: 12H)

EXAMPLE 38

Preparation of 1,5-diamino-3-oxapentane 1,5-Dichloro-3-oxapentane is treated with potassium phthalimid, followed by hydrazinolysis of the resulting diphthalimido-derivative and consecutive acidification whereby the bis-hydrochloride of the title compound is obtained.

The bis-hydrochloride is treated with a very concentrated (approx. 10N) solution of potassium hydroxide in water and continuously extracted with benzene in a liquid-liquid extractor for several (three to five) days. The solvent is evaporated and the liquid residue is distilled under reduced pressure giving the desire compound.
b.p.: 48° -50° /1mm Hg
Yield 30% (from the initial 1,5-dichloro-3-oxapentane).
PMR (CDCl$_3$): —NH$_2$: 1.30 ppm (singlet: 4H); —CH$_2$—N: 2.90 ppm (triplet: 4H); —CH$_2$—O: 3.50 ppm (triplet: 4H).

EXAMPLE 39

Preparation of diglycolic acid dichloride g.

To 13.4 g. of diglycolic acid covered with chloroform (150 ml.), 45 g. phosphorus pentachloride are added at once.

After standing for ten minutes at room temperature the mixture is heated slowly to reflux temperature over a period of one hour and is then left under reflux for 1.5 hours. The solvent is then evaporated at room temperature under reduced pressure (water pump.) Then, the phosphorus oxychloride formed during the reaction is taken off at room temperature under 0.5 mm Hg pressure (oil pump). The remaining oil is distilled (oil bath below 80° C.) giving 14.8 of the desired dichloride.
b.p. = 56°-57°/0.5 mm Hg.
Yield = 86%.
PMR (CDCl$_3$): O—CH$_2$—CO: 4.65 ppm (singlet).
The dichloride is unstable to heat and must be distilled at low temperature at sufficiently low pressure.

EXAMPLE 40

Preparation of 5,9-dioxo-1,7,13-trixoxa-4,10-diazacyclopentedecane

This reaction is carried out applying a high dilution technique. A solution of 29.6 g. of the diamine obtained in Example 2 (0.2 mole) in 1000 ml. anhydrous benzene and a solution of 17.2 g. (0.1 mole) of the dichloride obtained in Example 39 in 1000 ml. anhydrous benzene are added to 1,200 ml. anhydrous benzene over a period of eighteen hours under vigorous agitation and under nitrogen atmosphere. On termination, the benzene solution is filtered and evaporated to dryness. The crude solid residue is almost pure (m.p. 147°-148° C.). It is recrystallized from a hot mixture of tetrahydrofuran and heptane giving the title product.
m.p. = 149°-150° C.
Yield = 75%.

PMR (CDCl₃): N—CH₂—CH₂—O: 3.60 ppm (multiplet: 8H); O—CH₂—CH₂—O: 3.67 ppm (singlet: 4H): —CO—CH₂—O: 4.08 ppm (singlet: 4H); NH: 7.15 ppm (broad band: 2H).

EXAMPLE 41

Preparation of 1,7,13-Trioxa-4,10-diazacyclopentadecane

A solution of 15.7 g. of the diamide obtained in Example 40 in 300 ml. hot anhydrous tetrahydrofuran is slowly added to a mixture of 50 ml. anhydrous tetrahydrofuran and 15 g. LiAlH₄ while stirring over a period of 1.5 hours. After the addition is completed, the mixture is stirred under reflux and under a nitrogen atmosphere for twenty hours. After cooling to room temperature the excess reagent is destroyed by adding a mixture (45 ml.) of water and THF (1:2), followed by 15 ml. NaOH 15% and 45 ml. water. The mixture is filtered and the filtrate is evaporated to dryness. The residue is dissolved in benzene and the solution is passed through a column of Al₂O₃ with benzene as eluant. The solution is evaporated to dryness and a semicrystalline product is obtained (mixture of crystals and an oil) which proves to be the desired product.

Yield = 89%

PMR (CDCl₃): CH₂N: 2.75 ppm (triplet: 8H); Ch₂—O: 3.60 ppm (triplet + singlet: 12H)

EXAMPLE 42

Preparation of 2,9-dioxo-4,7,13,16,21-pentaoxa-1,10-diazabicyclo[8,8,5]tricosane The reaction is carried out applying the high dilution technique. A solution of 8.72 g. of the cyclic diamine obtained in Example 42 and 8.8 g. of triethylamine in 500 ml. anhydrous benzene and a solution of the dichloride (8.6 g. in 500 ml. anhydrous benzne) obtained in Example 1B is added to 1000 ml. anhydrous benzene during ten hours under nitrogen atmosphere and under agitation. The salt of triethylamine and the hydrochloric acid precipitates and is filtered off. The filtrate is evaporated to dryness. The residue is dissolved in benzene and passed through a column of Al₂O₃ (100 g.) using benzene as an eluant. The title compound is obtained as an oil which crystallizes on standing. The product is recrystallized from a hexane-benzene mixture. m.p. = 105° C.

Yield = 45%.

PMR (CDCl₃): several peaks between 3.3 and 4.6 ppm.

EXAMPLE 43

Preparation of 4,7,13,16,21-pentaoxa-1,10-diazabicyclo-[8,8,5]tricosane

A solution of 5 g. of the bicyclic diamide obtained in Example 42 in 50 ml. anhydrous tetrahydrofuran is slowly added to 50 ml. of the fresh prepared B₂H₆ solution (1.0M) under nitrogen atmosphere and at a temperature 0° C. The mixture is agitated at this temperature for thirty minutes and thereafter 1.5 hours at reflux temperature. The excess reagent is destroyed by adding 10 ml. of water and the solution is evaporated on a rotatory evaporator under vacuum. 3.5 g. of the diborane of the title compound is obtained (m.p. = 205°-209° C.).

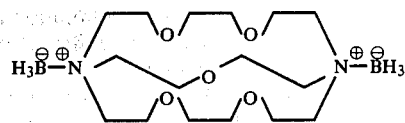

This compound is hydrolysed by adding 50 ml. 6N hydrochloricid acid under heating and a solution is obtained. The mixture is evaporated to dryness under vacuum on a rotary evaporator. The residue is dissolved in 30 ml. water and the solution is passed through a column of an anion exchange resin (Dowex 1, Trade Mark). The column is washed with water until there is no basic reaction. The water is evaporated. The title compound is obtained as a colourless oil (3 g.)

Yield = 95%

PMR (DCDl₃): —CH₂—N: 2.65 ppm (triplet: 12H); —CH₂—O: 3.60 ppm (triplet: 12H); 3.70 ppm (singlet: 8H).

EXAMPLE 44

Preparation of 5.9-dioxo-1,7-dioxa-4,10-diaza-cyclododecane

This reaction is carried out applying the high dilution technique. A solution of 10.4 g. of the diamine obtained in Example 38 (0.1 mole) in 100 ml. anhydrous benzene and a solution of 8.6 g. (0.05 mole) of the dichloride obtained in Example 30 in 100 ml. anhydrous benzene are added to 1000 ml, anhydrous benzene over a period of 50 minutes under vigorous agitation. The reaction mixture is filtered and the residue is dwashed with hot chloroform (3 × 500 ml.) the combined solutions are evaporated to dryness leaving a crystalline residue (m.p. = 180°-181° C.) which is recrystallized from a hot mixture of chloroform and heptane giving the desired product.

m.p. = 182°-183° C. Yield = 65%.

PMR (CDCl₃): N—CH₂—CH₂O: 3.60 ppm (broad multiplet: 8H) CO—CH₂—O: 4.15 ppm (singlet: 4H); NH: 7.65 ppm (broad band: 2H)

EXAMPLE 45

Preparation of 1,7-dioxa-4,10-diazacyclodecane a suspension of 5.0 g. of the diamide obtained in Example 44 in 100 ml. hot anhydrous tetrahydrofuran and 4.8 g. LiAlH₄ while stirring over a period of one hour. After the addition is completed, the mixture is stirred under reflux and under a nitrogen atmosphere for eighteen hours. After cooling to room temperature the excess reagent is destroyed by adding a mixture (15 ml.) of water and THF (1:2) followed by 5 ml. NaOH 15% and 15ml. water. The mixture is filtered and the filtrate is evaporated to dryness. The residue is dissolved in benzene and the solution is passed through a column of Al₂O₃ with benzene as eluant. The solution is evaporated to dryness and after recrystallization from hot benzene/heptane the desired product is obtained.

m.p. = 83°-84° C. Yield = 70%.

PMR (CDCl₃): NH: 2.40 ppm (singlet: 2H); —CH₂—N: 2.80 ppm (triplet: 8H); —CH₂—O: 3.66 ppm (triplet: 8H).

EXAMPLE 46

Strongly basic solutions

When solid potassium hydroxide is added to a solution of 4,7,13,16,21,24-hexaoxa-1,10-diaza-bicyclo[8,8,8]-hexacosane (obtained in Example 6) in anhydrous tetrahydrofuran, a very strongly basic solution is obtained as KOH dissolves in the solvent under complex formation with the bicyclic diamine.

The strong basicity may be shown by adding some fluorene: an intense red colour, due to the formation of the fluorenyl anion, develops immediately. By treating this strongly basic solution with oxygen (or air), fluorenone is obtained. When no bicyclic amine is present the anion is not formed and the solution remains colourless.

The same observations may be made when KOH is replaced by another base such as sodamide.

EXAMPLE 47

Purification of Tetraglycolic acid

A. Preparation of tetraglycolic acid dianilid

Tetraglycolic acid dichloride is prepared as described in Example 13. 22 g. of this dichloride in 50 ml. anhydrous benzene are treated at 0° C. (ice bath) with 35 g. aniline in 50 ml. anhydrous benzene. The mixture is heated to 60° C. for ten minutes and is poured into a separation funnel; 200 ml. water and 200 ml. chloroform are then added. The organic layer is separated and washed with 200 ml. 5% hydrochloric acid and then with 200 ml. water.

The solution is dried over sodium sulfate and the solvents are evaporated. The dianilide thus obtained is an oil which is recrystallized:

(1) first from acetone-water (dissolved in hot acetone; water added until the mixture becomes cloudy);

(2) then from acetone-hexane (dissolved in hot acetone; hexane added until cloudy) using a crystal from (1) to initiate crystallization (m.p. 56° C.)

(3) finally again from acetone-water; a white crystalline product (19 g.) containing one mole of water, is thus obtained, m.p. 58° C. Yield = 60%

PMR (CDCl$_3$): O—CH$_2$—CH$_2$—O: 3.75 ppm (singlet: 8H); O—CH$_2$—CO: 4.06 ppm (singlet: 4H); aromatic protons: 7.0–7.6 ppm (multiplet: 10H).

All signals are sharp; no impurities present.

B. Hydrolysis of the dianilid 19 g. Of the dianilid obtained previously are suspended in 200 ml. 15% sodium hydroxide in water. The mixture is refluxed for approx. twenty hours. After cooling to room temperature, the liquid mixture (the aniline formed forms an upper layer) is washed three times with 150 ml. benzene. The water layer is then brought to pH 1 using 10% hydrochloric acid and evaporated first at the water pump and then at the oil pump while heating on the steam bath. The residue (NaCl + tetraglycolic acid) is washed with acetone, filtered and the solid on the funnel is washed two times with acetone. The acetone solution is evaporated to dryness. The oily residue obtained is pure tetraglycolic acid; PMR spectrum as described in Example 13A; small peaks due to contaminating compounds have completely disappeared (purity approx. 99%)

Yield = 90%

EXAMPLE 48

Preparation of 17,24-dioxo-4,7,13,16-tetraoxa-1,10-diazabicyclo[8,8,8-]hexacosane The reaction is carried out applying the high dilution technique. A solution of 10.48 g. of the cyclic diamine obtained in Example 4 and 8.8 g. of triethylamine in 300 ml. anhydrous benzene and a solution of the dichloride of octane-1,8-dicarboxylic acid (8.44 g. in 500 ml. anhydrous benzene) is added to 1200 ml. anhydrous benzene during ten hours under nitrogen atmosphere and under agitation. The salt of triethylamine and the hydrochloric acid precipitates and is filtered off. The filtrate is evaporated to dryness.

The product is an oil which crystallizes on standing. m.p. = 96°–98° C.

Yield = 45%,

PMR (CDCl$_3$): —(CH$_2$)$_6$—: 1.4–2.0 ppm (broad peaks: 12H); CH$_2$—N and CH$_2$—O: several peaks between 3.3 and 4.6 ppm.

EXAMPLE 49

Preparation of 4,7,13,16-tetraoxa-1,10-diazabicyclo-[8,8,8]hexacosane

A solution of 7 g. of the bicyclic diamide obtained in Example 48 in 80 ml. anhydrous tetrahydrofuran is slowly added to 70 ml. of the fresh prepared B$_2$H$_6$ solution (1.0M) under nitrogen atmosphere and at a temperature of 0° C. The mixture is agitated at this temperature for thirty minutes and thereafter 1.5 hour at reflux temperature. The excess reagent is destroyed by adding 20 ml. of water and the solution is evaporated on a rotary evaporator under vacuum. 6 g. of the diborane of the title compound is obtained (m.p. = 139° C.)

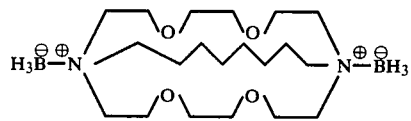

This compound is hydrolysed by adding 100 ml. 6N hydrochloric acid under heating and a solution is obtained. The mixture is evaporated to dryness under vacuum on a rotatory evaporator. The residue is dissolved in 20 ml. water and the solution is passed through a column of an anion exchange resin (Dowex 1, Trade Mark). The column is washed with water until there is no basic reaction. The water is evaporated. The title compound is obtained as a white crystalline solid.

m.p. = 90°–91° C.

Yield = 85%.

PMR (CDCl$_3$): —(CH$_2$)$_6$—: 1.4 ppm (broad peak: 12H); —CH$_2$—N: 2.40 ppm (broad peak: 4H); 2.65 ppm (triplet: 8H); —CH$_2$—O: 3.53 ppm (triplet: 8H); 3.70 ppm (singlet: 8H).

EXAMPLE 50

Preparation of the KSCW-complex of 4,7,13,16,21-pentaoxa-1,10-diazabicyclo[8,8,5] tripentacosane 100 mg. Of the macrocyclic compound obtained in Example 43 are dissolved in chloroform and an excess solid KSCN is added. After standing overnight at room temperature the mixture is filtered and the solution is evaporated to dryness. The residue is crystallized from an ether-acetone mixture. The crystalline complex melts at 131°–132° C.

EXAMPLE 51

Preparation of the Ba(SCN)$_2$-complex of 4,7,10,16,19,24,27-heptaoxa-1,13-diazabicyclo[8,8,11-]nonacosane 70 mg. Of the macrocyclic compound obtained in Example 22 and 70 mg. solid Ba(SCN)$_2$, H$_2$O are refluxed in 20 ml. acetone for five minutes. The acetone is then removed under vacuum and the residue is treated with 25 ml. chloroform. After filtration, the chloroform is evaporated and the residue is crystalized from a chloroform-benzene-ether mixture. A crystalline complex is obtained.

m.p. = above 260° C.

EXAMPLE 52

Further complexes of 4,7,13,16,21,24-hexaoxa-1,10-diazabicyclo[8,8,8]hexacosane

The following complexes of the macrocyclic obtained in Example 6 have been obtained by the method already described in Example 11, or else their formation has been observed by spectroscopic methods:

TlHCOO complex (m.p. = 50°-52° C.)
Ca(SCN)$_2$ complex (m.p. = above 260° C.)
Zn(BF$_4$)$_2$
Pb(SCN)$_2$

EXAMPLE 53

Complexes of 4,7,13,16,21-pentaoxa-1,10-diazabicyclo-[8,8,5-tricosane

This compund, obtained in Example 43, gives stable complexes with various metal salts in particular it readily forms complexes with transition metal salts. The complexes of the following salts have been prepared by mixing methanol solutions of the salt and of the complexing agent and letting the complex crystallize out, or else their formation has been observed by spectroscopic methods:

KSCN, BaCl$_2$, Co(SCN)$_2$, Ni(BF$_4$)$_2$, Cu(BF$_4$)$_2$

EXAMPLE 54

Preparation of 2,9-dioxo-4,7,13,18-tetraoxa-1,10-diazabicyclo[5,5,8]eicosane

The reaction is carried out applying the high dilution technique. A solution of 8.7 g. of the cyclic diamine obtained in Example 45 and 11 g. of triethylamine in 200 ml. anhydrous chloroform and 300 ml. anhydrous benzene and a solution of the dichloride (10.8 g. in 500 ml. anhydrous benzene) obtained in Example 1B is added to 1000 ml. anhydrous benzene during eight hours under nitrogen atmosphere and under agitation. The solution is filtered and the solid residues are washed several times with benzene. The combined organic layers are evaporated to dryness leaving an oily residue which is then extracted three times with hot benzene (3 × 200 ml.) Evaporation of the benzene layers give a solid residue which is filtered in benzene solution through a column of alumina.

The solid obtained after evaporation of the solvent, is recrystallized from a benzene-heptane mixture. The desired product is obtained.

m.p. = 151°-152° C.
Yield = 45%.

PMR (CDCl$_3$): two very complex multiplets between 2.6 –3.2 ppm (4H) and 3.4 –4.8 ppm (20H).

EXAMPLE 55

Preparation of 4,7,13,18-tetraoxa-1,10-diazabicyclo[5,5,8]eicosane 22 ml. of a freshly prepared B$_2$H$_6$ solution (0.8 M) are added with a syringe to a suspension of 2.9 g. of the bicyclic diamide obtained in Example 54 in 20 ml. anhydrous tetrahydrofurane under nitrogen atmosphere and at a temperature of 0° C. The mixture is agitated at this temperature for thirty minutes and thereafter three hours at reflux temperature. The excess reagent is destroyed by adding 5 ml. of water and the solution is evaporated on a rotatory evaporator under vacuum. The residue is extracted several times with chloroform and the solution obtained is evaporated to dryness. 1.9 g. of the diborane of the title compound is obtained.

m.p. = 121°-122° C.
Yield = 98%.

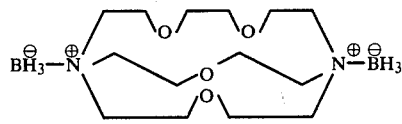

This compound (1.7 g.) is hydrolysed by adding 20 ml. 6N hydrochloric acid under heating (2.5hours) and a solution is obtained. The mixture is evaporated to dryness under vacuum on a rotatory evaporator. The residue is dissolved in 10 ml. water and the solution is passed through a column of an anion exchange resin (Dowex 1, Trade Mark). The column is washed with water until there is no basic reaction. The water is evaporated. The title compound is obtained as a colourless oil.

Overall yield = 95%.

PMR (CDCl$_3$): —CH$_2$—N: 2.75 ppm (triplet: 12H); —CH$_2$—O: 3.4-3.8 ppm (multiplet: 12H); 3.70 ppm (singlet: 4H).

EXAMPLE 56

Complexes of 4,7,13,18-tetraoxa-1,10-diazabicyclo[5,5,8]cicosane

Complex formation with the title compound (obtained in Example 55) has been observed spectrometrically (NMR) for the following salts:

Li Cl, Li SCN, Na Cl, K Br, K SCN, Ba Cl$_2$,Co(SCN)$_2$.

Some of these complexes are unstable in water. Strongly basic solutions have also been obtained by following the procedure of Example 46. Also here the formation of the fluorenyl anion has been observed when adding fluorene to an anhydrous tetrahydrofuran solution of the complex formed with KOH. When oxygen (or air) is bubbled through this strongly basic complex solution containing fluorenyl anion, fluorenone is obtained.

EXAMPLE 57

A. Preparation of 2-chloroethyl-chloromethyl ether 322 g. Of ClCH$_2$CH$_2$OH, cooled in ice-water, was saturated with gaseous HCl, and 120 g. of trioxymethylene was added, after which the solution was again saturated with HCl. The lower layer was separated, dried over CaCl$_2$, and dry CO$_2$ passed through the solution to remove excess HCl. Upon fractionation at reduced pressure the major portion $b_{23.7}65°-73°$. A small amount of trioxymethylene appears in the forerun. The yield is approx. 380 g.

B. Preparation of 2-chloroethoxy acetonitrile

Mixing of 315 g. of the product obtained in Example A and 250 g. copper cyanide $Cu_2(CN)_2$, followed by gentle heating, gives rise to a reaction which is controlled by cooling the flask with water. The reaction is finally completed by heating on a water bath for two hours. The reaction product is distilled at reduced pressure without removal of the $Cu_2(CN)_2$, yielding 250 g. of the title compound.

b.p. = 55°–58°/0.8 mm.

Yield = 85%.

C. Preparation of 2-chloroethyoxy acetic acid

This compound was prepared by treating 120 g. of the product obtained in Example 573 with 250 ml. of concentrated HCl. Reaction sets in after a short time, and it is necessary to cool the flask to control the reaction, which is finally completed by heating on a steam bath for two hours. The mixture is diluted with an equal volume of water, and extracted four times with 50 cc portions of ether. The ether is evaporated and the product is distilled in vacuum, $b_{3.5}130°$.

D. Preparation of monothio-triglycolic acid 9.2 g. (0.1 Mole) of thioglycolic acid are dissolved in a solution of 12 g. NaOH in 100 ml. water. 13.8 g. Of the product obtained in Example 57C are added slowly (over approx. fifteen minutes) and the mixture is heated to 80° C. for two hours. After cooling the solution is acidified with concentrated HCl and extracted three times with ether (3 × 50 ml.). The ether layers are combined, dried over sodium sulfate and evaporated to dryness. The title product (14.5 g.) is obtained as a very viscous oil.

Yield = 85%

PMR ($D_2O$): —S—$CH_2$—: 2.85 ppm (triplet; 2H); —S—$CH_2$—CO: 3.4 ppm (singlet: 2H); —O—$CH_2$—; 3.85 ppm (triplet: 2H); —O—$CH_2$—CO; 4.2 ppm (singlet: 2H).

E. Preparation of monothio-triglycolic acid dichloride

The dichloride of the diacid obtained in Example 57D is prepared using oxalyl chloride in the same way as described in Example 26B. The product is a viscous oil.

Yield = quantitative.

PMR ($CdCl_3$): —S—$CH_2$—: 2.85 ppm (triplet: 2H): —S—$CH_2$—CO—: 3.8 ppm (singlet: 2H); —O—$CH_2$—: 3.8 ppm (triplet: 2H); —O—$CH_2$—OH: 4.45 ppm (singlet: 2H)

EXAMPLE 58

Preparation of 2,9-dioxo-4,13,16-trioxa-7,21,24-trithia-1,10-diazabicyclo[8,8,8]hexacosane This reaction is carried out applying the high dilution technique. A solution of 4.5 g. of the diamine obtained in Example 29 and 2 g. triethylamine in 200 ml. anhydrous benzene and a solution of 3.8 g. of the dichloride obtained in Example 57E in 200 ml. anhydrous benzene are added to 1,200 ml. anhydrous benzene over a period of 2.5 hours under vigorous agitation and under a nitrogen atmosphere. On termination, the benzene solution is filtered and evaporated to dryness.

The oily residue is redissolved in benzene (100 ml.) and is filtered through a column of aluminium oxide (50 g.) The product is eluated with a mixture of chloroform and benzene (30%/70%). The solution is evaporated to dryness leaving a viscous oil, which is the desired compound (yield approx. 50%)

PMR ($CDCl_3$): very complex spectrum from 2.5 to 4.0 ppm; S—$CH_2$+$NCH_2$: from 2.5 to 2.9 ppm; O—$CH_2$: from 3.5 to 4.0 ppm.

EXAMPLE 59

Preparation of 4,13,16,trioxa7,21,24-trithia-1,10-diazabicyclo8,8,8]hexacosane 20 ml. of a solution (1.2 M) of diborane in anhydrous tetrahydrofuran are added to a solution of 1.5 g. of the bicylic diamide obtained in Example 58 in 20 ml. anhydrous tetrahydrofuran, under nitrogen atmosphere and at 0° C. The mixture is refluxed for two hours. The excess reagent is destroyed by adding 5 ml. of water and the solution is evaporated on a rotatory evaporator under vacuum. The residue is treated with 40 ml. 6N hydrochloric acid under reflux for two hours. The mixture is evaporated to dryness under vacuum on a rotatory evaporator. The residue is treated with a solution of tetraethylammonium hydroxide until a basic reaction is obtained. The mixture is extracted with benzene (3 × 50 ml.) and the organic layers are dried and filtered over a column of aluminium oxide. The solution is evaporated to dryness, leaving a viscous oil (1.4 g.), which is the desired compound.

Yield = 95%

PMR ($CDCl_3$): (—S—$CH_2$—) + (—N—$CH_2$—): 2.4–2.9 ppm (complex band: 24H; the —S—$CH_2$—$CH_2$—S group gives a singlet at 2.9 ppm); —O—$CH_2$—: 3.4–3.7 ppm (complex band: 12H)

EXAMPLE 60

21,24-Dimethyl-4,7,13,16-tetraoxa-1,10,21,24-tetraazabicyclo [8,8,8]hexacosane

A. Following the procedure of Example 3, 3,6-dimethyl-3,6-diaza1,8-octane-diamine is reacted with the dichloride obtained in Example 1B, to give 10,13-dimethyl-6,17-dioxo-1,4-dioxa-7,10,13, 16-tetraazacyclooctadecane.

B. The product of step A is reduced at the oxo-groups, following the procedure of Example 4 to give 10,13-dimethyl-1,4-dioxa-7,10, 13,16-tetraaza-cyclooctadecane.

C. Following the procedure of Example 5 the product of step B is condensed with the dichloride of Example 1B to give 21,24-dimethyl2,9-dioxo-4,7,13,16-tetraoxa-1,10,21,24-tetraaza-bicyclo[8,8,8]hexaxosane.

D. Reduction of the oxo-groups following the procedure of Example 6 gives the title compound.

EXAMPLE 61

Preparation of 1,2-di-(chlorocarbonylmethoxy)-benzene

A. 1,2-di-(carboxymethoxy)-benzene.

200 g. sodium hydroxide (5 mol) in 200 ml. water and 110 g. pyrocatechol (1 mole) are mixed in a 1 liter flask. 189 g. Of monochloroacetic acid (2 mol) are added slowly over a period of 3 hours. The mixture is heated to 100° over a period of 2 hours. After cooling, hydrochloric acid (100 ml.) are added, the acid precipitates and is recrystallized in water;

m.p.: 177° C.

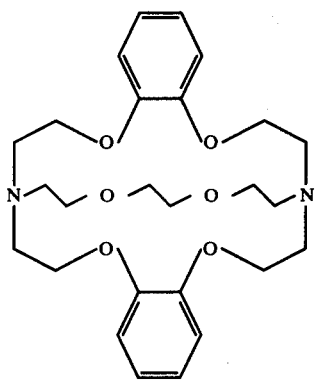

EXAMPLE 65

4,11,17,22-Tetraoxa-1,14-Diazatricyclo[12,5,5,0$^{5,10}$]tet-racosa-5,7,9-triene A. 2,13-dioxo-4,11,17,22-tetraoxa-1,14-diazatricyclo[12,5,5,0$^{5,10}$]tetracosa-5,7,9-triene In a manner similar to that described in Example 5, treat the cyclic diamine obtained in Example 45 and triethylamine in anhydrous benzene with 1,2-di-(chlorocarbonylmethoxy)-benzene (compound of Example 61) utilizing high dilution technique. Isolate and purify the resultant product in a manner similar to that described in Example 5 to obtain 2,13-dioxo-4,11,17,22-tetraoxa-1,14-diazo-tricyclo[12,5,5,0$^{5,10}$]tetracosa-5,7,9-triene.

B. 4,11,17,22-Tetraoxa-1,14-Diazatricyclo[12,5,5,0$^{5,10}$]tetracosa-5,7,9-triene In a manner similar to that described in Example 6, treat a solution of the bicyclic diamide obtained as described in Example 65A in tetrahydrofuran with freshly prepared boronhydride solution and isolate the resultant diborane derivative of 4,11,17,22-tetraoxa-1,14-diaza-tricyclo[12,5,5,0$^{5,10}$]-tetracosa-5,7,9-triene. Hydrolyze the diborane derivative with hydrochloric acid, then isolate the resultant product in a manner similar to that described in Example 6 to obtain 4,11,17,22-tetraoxa-1,14-diaza-tricyclo[12,5,5,0$^{5,10}$]-tetracosa-5,7,9-triene, having the following structural formula:

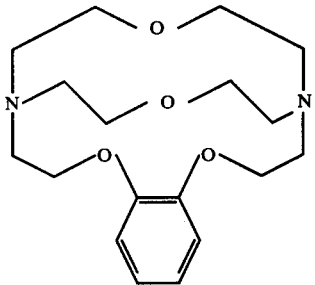

as a crystalline solid, m.p. 119°-120° C.

EXAMPLE 66

N,N'-Ditosylpolymethylenediamine-N,N'-Diacetyl Dichloride

A. N,N'-Ditosylethylenediamine-N,N'-diacetyl dichloride (1) Treat ethylenediamine with p-toluenesulfonyl chloride (i.e. tosyl chloride) and sodium hydroxide in aqueous ether according to known procedures to obtain N,N'-ditosylethylenediamine.

(2) Treat N,N'-ditosylethylenediamine with sodium in absolute ethanol methanol followed by treatment of the disodium salt thereby formed with bromoacetic acid methyl ester according to known procedures to obtain N,N'-ditosylethylenediamine-N,N'-diacetic acid dimethyl ester.

(3) Treat N,N'-ditosylethylenediamine-N,N'-diacetic acid dimethyl ester with acetic acid and concentrated hydrochloric acid accordng to known procedures followed by treatment of the thereby formed N,N'-ditosylethylenediamine-N,N'-diacetic acid with thionyl chloride to obtain N,N'-ditosylethylenediamine-N,N'-diacetyl dichloride.

B. N,N'-Ditosyltrimethylenediamine-N,N'-diacetyl dichloride

Follow procedures outlined in Example 66A, but utilize trimethylenediamine as starting compound instead of ethylenediamine to obtain N,N'-ditosyltrimethylenediamine-N,N'-diacetyl dichloride.

C. N,N'-Ditosyltetramethylenediamine-N,N'-diacetyl dichloride

Treat tetramethylenediamine in a manner similar to that described in above Example 66A to obtain N,N'-ditosyltetramethylenediamine-N,N'-diacetyl dichloride.

D. N,N'-Ditosylpentamethylenediamine-N,N'-diacetyl dichloride

Following the procedure outlined in above Example 66A, but utilize as starting compound pentamethylenediamine instead of ethylenediamine to obtain N,N'-ditosylpentamethylenediamine-N,N'-diacetyl dichloride.

E. N,N'-Ditosylhexamethylenediamine-N,N'-diacetyl dichloride

Follow the procedure outlined in above Example 66A, but utilize as starting compound hexamethylenediamine instead of ethylenediamine to obtain N,N'-ditosylhexamethylenediamine-N,N'-diacetyl dichloride.

EXAMPLE 67

4,7-Ditosyl-2,9-dioxo-16,13,21,24-tetraoxa-1,4,7,10-tetraazabicyclo[8,8,8]hexacosane Utilizing high dilution technique, in a manner similar to that described in Example 5, treat the cyclic diamine obtained in Example 4 with N,N'-ditosylethylenediamine-N,N'-diacetyl dichloride (compound of Example 66A), to obtain 4,7-ditosyl-2,9-dioxo-13,16,21,24-tetraoxa-1,4,7,10-tetraazabicyclo [8,8,8]hexacosane. Purify by filtering through a column of alumina, using benzene as eluant. Evaporate the benzene eluate to a residue and recrystallize the residue from benzene-hexane m.p. 208° C.

EXAMPLE 68

Tetraoxatetraaza Bicyclic Alkanes

A. 21,24-ditosyl-4,7,13,16-tetraoxa-1,10,21,24-tetraazabicyclo[8,8,8]hexacosane

In a manner similar to that described in Example 6, treat a solution of the bicyclic diamide obtained in Example 67 in tetrahydrofuran with freshly prepared boron hydride solution and isolate the resultant diborane derivatives of 21,24-ditosyl-4,7,13,16-tetraoxa-1,10,21,24-tetraazabicyclo[8,8,8]hexacosane, m.p. 216°-220° C. Hydrolyze the diborane derivative with 6N hydrochloric acid at reflux temperature for two hours, then treat the resulting dihydrochloride acid salt Yield: 50%.

PMR (basic (NaOH)D$_2$O; —O—CH$_2$—: 4.40 ppm (singlet; 4H) aromatic protons: 6.9 ppm (multiplet; 4H).

B. Acid dichloride 30 g. Of the above acid are added to a mixture of 200 ml. anhydrous benzene. Then 35 g. oxalylchloride are added, the flask being protected by a calcium chloride tube. The mixture is stirred for four days and the diacid progressively dissolves as it is being transformed into the corresponding dichloride. The solution is then evaporated to dryness (without heating) leaving a brownish solid residue which is recrystallized from a mixture of chloroform-benzene giving white crystals.

m.p. = 50° C.
Yield = 80%.

PMR (CDCl$_3$); —O—CH$_2$—COCl—; 5 ppm (singlet: 4H) aromatic protons: 7 ppm (singlet: 4H).

EXAMPLE 62

Preparation of 2,13-dioxo-4,11,17,20,25,28-hexaoxa-1,14-diazatricyclo[12,8,8,0$^{5,10}$]triaconta-5,7,9-trione This reaction is carried out applying the high dilution technique. A solution of 5.2 g. of the diamine obtained in Example 4, and 5 g. of triethylamine in 300 ml. anhydrous benzene; and a solution of 5.4 g. of the di-acid chloride obtained in Example 61 in 300 ml. anhydrous benzene, are added to 1000 ml. benzene during six hours under nitrogen atmosphere and under agitation. The triethylamine hydrochloride precipitates and is filtered off. The filtrate is evaporated to dryness. The residue is dissolved in benzene and passed through a column of Al$_2$O$_3$ (20 g.) using benzene as an eluant. The solutions are evaporated to dryness. The product is a viscous oil.

Yield = 50%.

PMR (CDCl$_3$); CH$_2$—N and CH$_2$O;, 2.5 to 4.5 ppm (complex multiplet: 24H): O—CH$_2$—CO: 5.0 ppm (AB system) aromatic protons: 7.0 ppm (singlet: 4H).

By substituting 3-methylpyrocatechol or 4-methylpyrocatechol in the above procedure of Example 61 there is obtained 1,2-di(chlorocarbonylmethoxy)-3-methylbenzene and 1,2-di-(chlorocarbonylmethoxy)-4-methylbenzene, respectively.

EXAMPLE 63

Preparation of 4,11,17,20,25,28-hexaoxa-1,14-diazo-tricyclo [12,8,8,0$^{5,10}$]triconta-5,7,9-triene 35 ml. of a freshly prepared solution (1.2 M) of diborane are added slowly to a solution of 3 g. of the amide obtained in Example 62 in 20 ml. anhydrous tetrahydrofuran under nitrogen atmosphere and at a temperature of 0° C. The mixture is then heated to reflux for two hours. The excess reagent is destroyed by slowly adding 5 ml. of water. The solution is evaporated to dryness on a rotatory evaporator under vacuum.

60 ml. 6H Hydrochloric acid are added to the residue and the mixture is refluxed for two hours. The solution is then evaporated to dryness under vacuum. The residue dissolved in 30 ml. water and the solution is passed through a column of an anion exchange resin (Dowex 1, Trade Mark). The column is washed with water until there is no basic reaction. The combined water solutions obtained are evaporated to dryness under vacuum on a water bath. The residue is a viscous oil.

Yield = 80%.

PMR (CDCl$_3$); —CH$_2$—N; 2.72 ppm (triplet: 8H), 2.90 ppm (triplet: 4H): —CH$_2$—O: 3.55 ppm (singlet: 8H and triplet: 8H): —CH$_2$—O (phenolic): 4.10 ppm (triplet: 4H): aromatic protons: 6.85 ppm (singlet: 4H).

64

4,11,17,24,32-Hexaoxa-1,14-diazo-tetracyclo[12,12,8,0$^{5,10,18,23}$]tetratriaconta-5,7,9,18,20,22-hexaene A. 5,16-dioxo-1,7,14,20-tetraoxa-4,17-diaza-bicyclo[12,8,0$^{8,13}$]docasa-8,10,12-triene In a manner similar to that described in Example 3 treat, utilizing high dilution technique, a solution of 1,8-diamino-3,6-dioxaoctane (compound of example 2) in anhydrous benzene with a solution of 1,2-di-(chlorocarbonylmethoxy)-benzene (compound of Example 61) in benzene. Isolate and purify the resultant product in a manner similar to that described in Example 3 to obtain 5,16-dioxo-1,7,14,20-tetraoxa-4,17-diazobicyclo[12,8,0$^{8,13}$]docasa-8,10,12-triene.

B. 1,7,14,20-tetraoxa-4,17-diaza-bicyclo[12,0,0$^{8,13}$]docasa-8,10,12-triene

In a manner similar to that described in Example 4 treat a solution of the diamide obtained in above Example 64A in tetrahydrofuran with lithium aluminum hydride. Isolate and purify the product in a manner similar to that described in Example 4 to obtain 1,7,14,20-tetraoxa-4,17-diazo-bicyclo[12,8,0$^{8,13}$]docasa-8,10,12-triene.

C. 2,13-Dioxo-4,11,17,24,29,32-hexaoxa-1,14-diazatetracyclo-[12,12,8,0$^{5,10,18,23}$]tetratriaconta-5,7,9,18,20,22-hexaene In a manner similar to that described in Example 5 treat, applying high dilution technique, the cyclic diamine obtained as described in above Example 64B with the di-acid chloride obtained as described in Example 61B in anhydrous benzene under nitrogen atmosphere. Isolate and purify the resultant product in a manner similar to that described in Example 5 to obtain 2,13-dioxo-4,11,17,24,29,32-hexaoxa-1,14-diaza-tetracyclo12,12,8,0$^{5,10,18,23}$]tetratriaconta-5,7,9,18,20,22hexaene.

D. 4,11,17,24,29,32-Hexaoxa-1,14-diazo-tetracyclo[12,12,8,0$^{5,10,18,23}$]tetratriaconta-5,7,9,18,20,22-hexaene In a manner similar to that described in Example 6 treat a solution of the bicyclic diamide obtained as described in above Example 64C in tetrahydrofuran with freshly prepared boron hydride solution. Isolate the resultant diboron, hydrolyze the diboron with hydrochloric acid, then isolate and purify the resultant product in a manner similar to that described in Example 6 to obtain 4,11,17,24,29,32-hexaoxa-1,14-diaza-tetracyclo[12,12,8,0$^{5,10,18,23}$]tetratriaconta-5,7,9,18,20,22-hexaene as a viscous liquid having the following structural formula:

with tetramethylammonium hydroxide followed by extraction with ether. Evaporate the ether extracts in vacuo to a residue comprising 21,24-ditosyl-4,7,13,16-tetraoxa-1,10,21,24-tetraazabicyclo[8,8,8]hexacosane, m.p. 83°-84° C., having the following structural formula:

hydrochloride salt with tetramethylammonium hydroxide in a manner similar to that described in Example 68A to obtain the corresponding ditosyltetraoxatetraazabicyclic macrocyclics of 68C(1) through 68C(4) as shown below.

D. Treat each of the ditosyltetraoxatetraazabicyclic macrocyclics prepared as described in above Example 68C with lithium in liquid ammonia to obtain the corresponding tetraxoatetraaxabicyclic macrocyclics of structural formulae 68D(1) through 68D(4) as shown below.

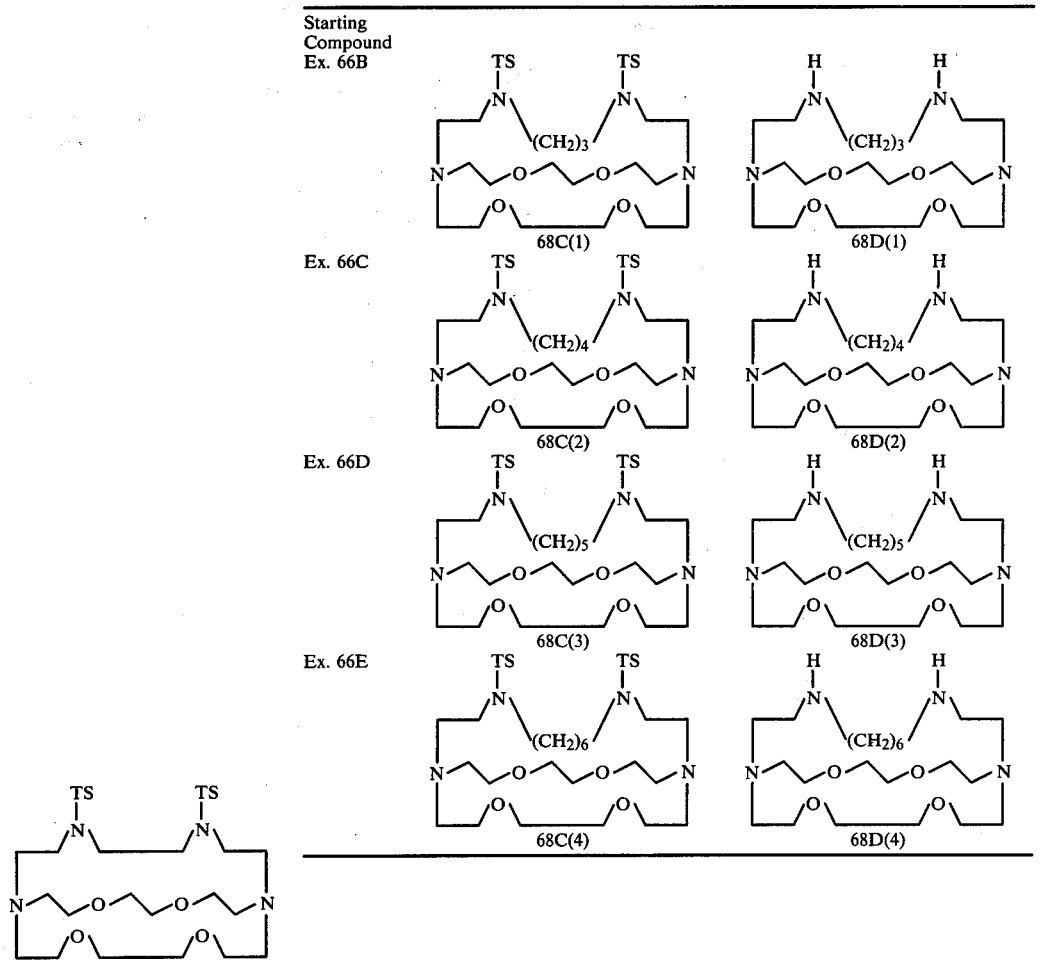

B. 4,7,13,16-Tetraoxa-1,10,21,24-tetraazabicyclo[8,8,8]-hexacosane

Treat the 4,7-ditosyltetraazabicyclohexacosane prepared in above Example 68A with lithium in liquid ammonia in a manner similar to that described in Example 4. Isolate the resultant product in a manner similar to that described in Example 4 to obtain 4,7,13,16-tetraoxa-1,10,21,24-tetraazabicyclo[8.8.8]hexacosane. Then purify by sublimation (50° C., 0.01 mm.Hg) or by recrystallization in hexane, m.p. 69° C.

C. Treat each of the N,N'-ditosylpolymethylenediamine-N,N'-diacetyl dichlorides prepared as described in Examples 66B through 66E with the cyclic diamine obtained in Example 4 in the manner described in Example 67 followed by treatment of each of the resulting bicyclic diamides with boronhydride according to the procedure described in Example 68A followed by hydrolysis of the thereby formed diborane derivative with hydrochloric acid and thence neutralization of the di-

EXAMPLE 69

7,10-Ditosyl-1,16-dioxa-4,7,10,13-tetraazacyclooctadecane

A. 7,10-Ditosyl-5,12-dioxo-1,16-dioxa-4,7,10,13-tetraazacyclooctadecane

In a manner similar to that described in Example 3, treat 1,8-diamino-3,6-dioxaocatne (Example 2C) with N,N'-ditosylethylenediamine-N,N'-diacetyl dichloride of Example 66A in benzene utilizing high dilution techaniques to obtain the 7,10-ditosyl-5,12-dioxo-1,16-dioxa-4,7,10,13-tetraazacyclooctadecane.

B. 7,10-Ditosyl-1,16-dioxa-4,7,10,13-tetraazacyclooctadecane

In a manner similar to that described in Example 6, treat a solution of the cyclic diamide obtained in Example 69A in tetrahydrofuran with boron hydride and isolate the resultant diborane derivative of 7,10-ditosyl-1,16-dioxa-4,7,10,13-tetraazacyclooctadecane, m.p. 216° C. Hydrolyze the diborane derivative with hydrochloric acid followed by treatment of the dihydrochloride salt with tetramethylammonium hydroxide in the manner of Example 6 to obtain 7,10-ditosyl-1,16-dioxa-4,7,10,13-tetraazaxyclooctadecane, m.p. 121° C.

EXAMPLE 70

21,24-Dioxa-1,4,7,10,13,16-hexaazabicyclo[8,8,8]hexacosane

A. 4,7,13,16-Tetratosyl-2,6-dioxo-21,24-dioxa-1,4,7,10,13,16-hexaaxzabicyclo8,8,8]hexacosane In a manner similar to that described in Example 5, treat the cyclic diamine obtained in Example 69B with the diacetyldichloride obtained in Example 66A to obtain 4,7,13,16-tetratosyl-2,6-dioxo-21,24-dioxa-1,4,7,10,13,16-hexaazabicyclo[8,8,8]hexacosane, m.p. =188° C.

B. 4,7,13,16-Tetratosyl-21,24-dioxa-1,4,7,10,13,16-hexaazabicyclo[8,8,8]hexacosane Treat the dicarboxamide-tetratosylamide macrobicyclic compound of Example 70A with boron hydride and tetrahydrofuran in the manner of Example 6 to obtain the diborane derivative of 4,7,13,16-tetratosyl-21,24-dioxa-1,4,7,10,13,16-hexaazabicyclo[8,8,8]hexacosane. Hydrolyze with 6N hydrochloric acid at reflux temperature for two hours, then treat the resultant hydrochloride salt with tetramethylammonium hydroxide to give 4,7,13,16-tetratosyl-21,24-dioxa-1,4,7,10,13,16-hexaazabicyclo[8,8,8]hexacosane, m.p. =104°-107° C.

C. 21,24-Dioxa-1,4,7,10,13,16-hexaazabicyclo[8,8,8-]hexacosane

In a manner similar to that described in Example 4, treat the 4,7,13,16-tetratosylhexaazabicyclohexacosane of Example 70B with lithium in liquid ammonia to obtain 21.24-dioxa-1,4,7,10,13,16-hexaazabicyclo[8,8,8-]hexacosane, m.p. = 75° C., having the following structural formula:

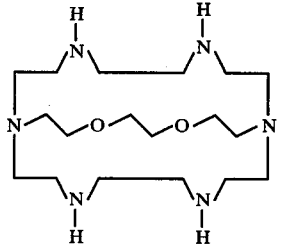

D. In above procedure 70A, by substituting for the N,N'-ditosylethylenediamine, N,N'-diacetyl dichloride of Example 66A, other diotsylpolymethylenediaminediacetyl dichlorides prepared as described in Examples 66B through 66E, there is obtained the corresponding dioxotetratosyldioxanexaazabicycloalkane which, when treated in the manner described in above Example 70A through 70D, yields the corresponding dioxahydexaazabicycloalkane.

EXAMPLE 71

13,18-Dioxa-1,4,7,10-tetraazabicyclo[8,5,5]eicosane

A. 4,7-Ditosyl-2,9-dioxo-13,18-dioxa-1,4,7,10-tetraazabicyclo[8,5,5]eicosane

In a manner similar to that described in Example 3, treat the cyclic diamine prepared in Example 45 with the N,N'-ditosylethylenediamine-N,N'-diacetyl dichloride of Example 66A in benzene under high dilution techniques to obtain 4,7-ditosyl2,9-dioxo-13,18-dioxa-1,4,7,10-tetraazabicyclo[8,5.5]eicosane.

B. 4,7-Ditosyl-13,18-dioxa-1,4,7,10-tetraazabicyclo[8,5,5]eicosane

In a manner similar to that described in Example 6, treat the bicyclicdiamide obtained in Example 71A in tetrahydrofuran with boron hydride followed by hydrolysis of the resulting diborane derivative with hydrochloric acid and thence treatment of said hydrochloride salt with tetramethylammonium hydroxide to obtain 4,7-ditosyl-13,18-dioxa-1,4,7,10-tetraazabicyclo[8,5,5]eicosane.

C. 13,18-Dioxa-1,4,7,10-tetraazabicyclo[8,5,5]eicosane

In a manner similar to that described in Example 4, treat the 4,7-ditosyltetraazabicycloeicosane obtained in Example 71B with lithium in liquid ammonia. Isolate the resultant product in a manner similar to that described to obtain 13,18-dioxa-1,4,7,10-tetraazabicyclo[8,5,5]eicosane, having the following structural formula:

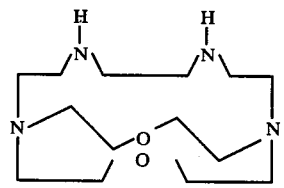

EXAMPLE 72

4,7-Ditosyl-13,16,19-trioxa-1,4,7,10-tetraazacycloheneicosane

A. 7,10-Ditosyl-5,12-dioxo-1,16,19-trioxa-4,7,10,13-tetraazacycloheneicosane

In a manner similar to that described in Example 3, treat the diaminotrioxaalkane derivative prepared in Example 14C with the N,N'-ditosylethylenediamine-N,N'-diacetyl dichloride prepared in Example 66A in benzene under high dilution techniques to obtain 7,10-ditosyl-5,12-dioxo-1,16,19-trioxa-4,7,10,13-tetraazacycloheneicosane.

B. 4,17-Ditosyl-13,16,19-trioxa-1,4,7,10-tetraazacycloheneicosane

In a manner similar to that described in Example 6, treat the bicyclic diamine of Example 72A in tetrahydrofuran with boron hydride followed by hydrolysis of the resultant diborane derivative thereby produced with hydrochloric acid followed by treatment of the thereby formed hydrochloride salt with tetramethylammonium hydroxide to obtain 4,17-ditosyl-13,16,19-trioxa-1,4,7,10-tetraazacycloheneicosane.

EXAMPLE 73

4,10,13,16-Tetraoxa-1,7,21,24-tetraazabicyclo[5,11,8]hexacosane

A. 21,24-Ditosyl-2,6,dioxo-4,10,13,16-tetraoxa-1,7,21,24-tetraazabicyclo[5,11,8]hexacosane In a manner similar to that described in Example 3, treat the cyclic diamine prepared in Example 72 with the diacid dichloride prepared in Example 39 in benzene under high dilution techniques to obtain 21,24-ditosyl-2,6-dioxo-4,10,13,16-tetraoxa-1,7,21,24-tetraazabicyclo[5,11,8]hexacosane.

B. 21,24-Ditosyl-4,10,13,16-tetraoxa-1,7,21,24-tetraazabicyclo[5,11,8]hexacosane In a manner similar to that described in Example 6, treat the bicyclic diamide obtained in Example 73A with boron hydride followed by hydrolysis of the resultant diborane derivative with 6N hydrochloric acid and thence treatment of the hydrochloride salt thereby formed with tetramethylammonium hydroxide to obtain 21,24-ditosyl-4,10,13,16-tetraoxa-1,7,21,24-tetraazabicyclo[5,11,8]hexacosane.

C. 4,10,13,16-Tetraoxa-1,7,21,24-tetraazabicyclo[5,11,8]hexacosane

In a manner similar to that described in Example 6, treat the tetraoxatetraazabicyclic compound of Example 73B with boron hydride to obtain 4,10,13,16-tetraoxa-1,7,21,24-tetrazabicyclo[5,11,8]hexacosane, having the following structural formula:

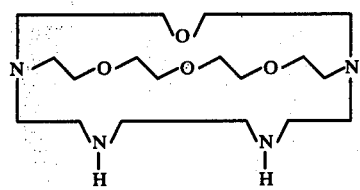

EXAMPLE 74

13,16-Dioxa-21,24-dithia-1,4,7,10-tetraazabicyclo[8,8,8]hexacosane

A. 4,7-Ditosyl-2,9-dioxo-13,16-dioxa-21,24-dithia-1,4,7,10-tetraazabicyclo[8,8,8]hexacosane In a manner similar to that described in Example 5, treat the cyclic diamine obtained in Example 29 with the N,N'-ditosylethylenediamine-N,N'-diacetyl dichloride prepared as described in Example 66A in benzene under high dilution techniques to obtain 4,7-ditosyl-2,9-dioxo-13,16-dioxa-21,24-dithia-1,4,7,10-tetraazabicyclo[8,8,8-]hexacosane.

B. 4,7-Ditosyl-13,16-dioxa-21,24-dithia-1,4,7,10-tetraazabicyclo-[8,8,8]hexacosane In a manner similar to that described in Example 6, treat the bicyclicidicarboxamideditosylamide prepared as described in Example 74A with boron hydride followed by hydrolysis of the resultant diborane derivative with 6N hydrochloric acid and thence treatment of the thereby formed hydrochloride salt with tetramethylammonium hydroxide to obtain 4,7-ditosyl-13,16-dioxa-21,24-dithia-1,4,7,10-tetraazabicyclo[8,8,8]hexacosane.

C. 13,16-Dioxa-21,24-dithia-1,4,7,10-tetraazabicyclo[8,8,8]-hexacosane

In a manner similar to that described in Example 4, treat the ditosylamidebicyclicdiamine compound prepared as described in Example 74B with lithium in liquid ammonia to obtain 13,16-Dioxa-21,24-dithia-1,4,7,10-tetraazabicyclo[8,8,8]-hexacosane having the following structural formula:

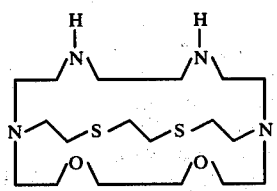

EXAMPLE 75

Ditosyltetrathiatetraazabicycloalkanes

A. 13,16,21,24-Tetrathia-1,4,7,10-tetraazabicyclo[8,8,8]-hexacosane

Treat the cyclic diamine prepared in Example 33 with N,N'-ditosylethylenediamine-N,N'-diacetyl dichloride prepared in Example 66A in the manner of Example 3 followed by treatment of the thereby formed 2,9-dioxo-4,7-ditostyl-13,16,21,24-tetrathia-1,4,7,10-tetraazabicyclo[8,8,8]hexacosane with boron hydride in the manner of Example 6 followed by hydrolysis of the diborane derivative thereby formed and thence treatment of the resulting hydrochloride salt with tetramethylammonium hydroxide to obtain 4,7-ditosyl-13,16,21,24-tetrathia-1,4,7,10-tetraazabicyclo-[8,8,8]hexacosane. Treat the foregoing 4,7-ditosylbicyclictetraazaalkane with lithium in liquid ammonia according to the procedure of Example 4 to obtain 13,16,21,24-tetrathia-1,4,7,10-tetraazabicyclo[8,8,8]hexacosane.

In the above procedure by substituting for the compound of Example 66A other diacetyl dichlorides prepared as described in Examples 66B through 55E respectively, there is obtained the following tetrathiatetraazabicycloalkanes, respectively:

(B). 14,17,22,25-tetrathia-1,4,8,11-tetraazabicyclo[9,8,8]heptacosane;
(C). 15,18,23,26-tetrathia-1,4,9,12-tetraazabicyclo[10,8,8]octacosane;
(D). 16,19,24,27-tetrathia-1,4,10,13-tetraazabicyclo[11,18,18]nonacosane; and
(E). 17,20,25,28-tetrathia-1,4,11,14-tetraazabicyclo[12,8,8]triacontane.

EXAMPLE 76

Alternate Procedure for the Preparation of 21,24-Dimethyl-4,7,13,16-tetraoxa-1,10,21,24-tetraazabicyclo[8,8,8]hexacosane (Compound of Example 60)

A. 21,24-Dicarbomethoxy-4,7,13,16-tetraoxa-1,10,21,24-tetraazabicyclo[8,8,8]hexacosane (1) In a manner similar to that described in Example 7, treat 4,7,13,16-tetraoxa-1,10,21,24-tetraazabicyclo[8,8,8]-hexacosane (compound of Example 68B) with methyl chlorocarbonate Isolate and purify the resultant product in a manner similar to that described in Example 7 to obtain 21,24-dicarbomethoxy-4,7,13,16-tetraoxa-1,10,21,24-tetraazabicyclo[8,8,8]hexacosane, m.p. =86° C.

(2) In the above procedure, by substituting ethyl chlorocarbonate and n-propyl chlorocarbonate for methyl chlorocarbonate, there is obtained the corresponding di-carboalkoxy derivatives, i.e. 21,24-dicarboethoxy and 21,24-dicarbopropyloxy-4,7,13,16-tetraoxa-1,10,21,24-tetraazabicyclo[8,8,8]hexacosane.

(3) In the procedure of Example 76A (1), by substituting ethylchloroacetate for methylchlorocarbonate, there is obtained the corresponding alkoxycarbonylmethylene derivative, i.e. 21,24-diethoxycarbonylmethylene 4,7,13,16-tetraoxa-1,10,21,24-tetraazabicyclo[8,8,8]hexacosane (i.e. the 21,24-di-($CH_2COOOC_2H_5$) derivative).

B. 21,24-Dimethyl-4,7,13,16-tetraoxa-1,10,21,24-tetraazabicyclo[8,8,8]hexacosane (1) In a manner similar to that described in Example 4, treat the 21,24-dicarbomethoxy-derivative prepared in Example 76A(1) with lithium aluminum hydride. Isolate and purify the resultant product in a manner similar to that described to obtain 21,24-dimethyl-4,7,13,16-tetraoxa-1,10,21,24-tetraazabicyclo-[8,8,8]hexacosane as a viscous liquid.

(2) In a similar manner, by reducing with lithium aluminum hydride the corresponding 21,24-ethyl chlorocarbonate and n-propylchlorocarbonate derivatives prepared as described in Example 17A(2) there is obtained the compound of this example, i.e. 21,24-dimethyl-4,7,13,16-tetraoxa-1,10,21,24-tetraazabicyclo-[8,8,8]hexacosane.

EXAMPLE 77

13,16,21,24-Tetramethyl-4,7-dioxa-1,10,13,16,21,24-hexaazabicyclo[8,8,8]hexacosane A.  13,16,21,24-Tetracarbomethoxy-4,7-dioxa-1,10,13,16,21,24-hexaazabicyclo[8,8,8]hexacosane (1) In a manner similar to that described in Example 7, treat 4,7-dioxa-1,10,13,16,21,24-hexaazabicyclo[8,8,8]hexacosane (compound of Example 70C) with methyl chlorocarbonate to obtain 13,16,21,24-tetracarbomethoxy-4,7-dioxa-1,10,13,16,21,24-hexaazabicyclo[8,8,8]hexacosane as a viscous liquid.

(2) By substituting ethyl chlorocarbonate or n-propyl-chlorocarbonate for methyl chlorocarbonate in the above procedure, there is obtained the corresponding 13,16,21,24-tetracarboethoxy or 13,16,21,24-tetracarbopropyloxy derivative, respectively.

(3) In the procedure of Example 77A(1), by using ethylchloroacetate instead of ethylchlorocarbonate, there is obtained 13,16,21,24-tetraethoxycarbonylmethylene-4,7-dioxa-1,10,13,16,21,24-hexaazabicyclo[8,8,8]hexacosane (i.e. the 13,16,21,24-tetra-(CH$_2$COOC$_2$H$_5$)derivative).

B.  13,16,21,24-Tetramethyl-4,7-dioxa-1,10,13,16,21,24-hexaazabicyclo[8,8,8]hexacosane (1) In a manner similar to that described in Example 4, treat the 13,16,21,24-tetracarbomethoxy compound prepared in Example 77A(1) with lithium aluminum hydride to obtain 13,16,21,24-tetramethyl-4,7-dioxa-1,10,13,16,21,24-hexaazabicyclo [8,8,8]hexacosane, m.p.=32°–33° C.

(2) In similar manner, by reducing with lithium aluminum hydride the 13,16,21,24-tetracarboethoxy or tetracarbopropyloxy derivatives prepared in Example 77A(2), there is obtained 13,16,21,24-tetramethyl-4,7-dioxa-1,10,13,16,21,24-hexaazabicyclo[8,8,8]hexacosane (the compound of this example).

EXAMPLE 78

Preparation of Pentaglycolyl Chloride

A. In a manner similar to that described in Example 1A, treat pentaethylene glycol with nitric acid to obtain pentaglycolic acid.

B. In a manner similar to that described in Example 1B, treat pentaglycolic acid with oxalyl chloride in anhydrous benzene in the presence of pyridine. Isolate and purify the resultant product in a manner similar to that described to obtain pentaglycolyl chloride having the following formula:

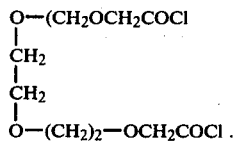

EXAMPLE 79

Preparation of 1,4-diamine-3,6,9,10-tetroaoxatetradecane

A. In a manner similar to that described in Example 2A, treat pentethylene glycol with phosphorous tribromide in pyridine. Isolate and purify the resultant product in a manner similar to that described to obtain pentaethylene glycol dibromide.

B. In a manner similar to that described in Example 2B, treat the pentaethylene glycol dibromide with phthalimide and potassium hydroxide in ethanol. Isolate and purify the resultant product in a manner similar to that described to obtain pentaethyleneglycol diphthalimide.

C. In a manner similar to that described in Example 2C, treat the pentaethylene glycol diphthalimide prepared as described in Example 79B with hydrazine in aqueous methanol. Isolate and purify the resultant product in a manner similar to that described to obtain 1,4-diamine-3,6,9,10-tetraoxatetradecane, having the following formula:

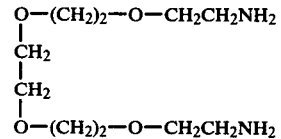

EXAMPLE 80

Polyoxadiazabicycloalkanes

Ex. 80(a)-A.
1,7,10,16,19,22-hexaoxa-4,13-diazacyclotetracosane

In a manner similar to that described in Example 3, and 4, treat 1,14-diamino-3,6,9,12-tetraoxatetradecane with tetraglycolyl chloride in benzene utilizing high dilution technique. Then treat the thereby formed 5,12-dioxo-1,7,10,16,19,22-hexaoxa-4,13-diazacyclotetracosane with lithium aluminum hydride in tetrahydrofuran to obtain 1,7,10,16,19,22-hexaoxa-4,13-diazacycloteracosane.

Ex. 80(a)-B.
4,7,13,16,21,24,27,30-Octaoxa-1,10-diazabicyclo-[8,8,8]dotriacontane In a manner similar to that described in Examples 5 and 6, treat the polyoxacyclicdiamine prepared in Example 80(a)-A with triglycolyl chloride in benzene utilizing high dilution techniques and thence treat the resulting 2,9-dioxo-4,7,13,16,21,24,2,30-octaoxa-1,10-diazabicyclo[8,8,14]dotriacontane with boron hydride in tetrahydrofuran followed by hydrolysis of the resulting diborane derivative with 6N hydrochloric acid and then treatment of the hydrochloride salt thereby formed with tetramethylammonium hydroxide to obtain 4,7,13,16,21,24,27,30-octaoxa-1,10-diazabicyclo-[8,8,14]dotriacontane.

Ex. 80(b)-80(n).

In a manner similar to that described in Example 80(a)-A and 80(a)-B, treat each of the following polyglycolyl chlorides with each of the following polyoxadiaminoalkanes to obtain a polyoxadiazacycloalkane product A as indicated, followed by treatment thereof with a polyglycolyl chloride (or polythioglycolyl chloride) to obtain a polyoxadiazabicycloalkane B as indicated hereinbelow.

In the following table, the structural formulae of the compounds are indicated diagramatically, it being understood there is an ethylene bridge between each of the hetero atoms indicated and that the structures are cyclic and bicyclic respectively with nitrogen being the bridgehead atom. Thus,

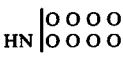 is equivalent to

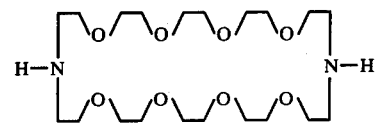

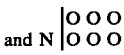 is equivalent to

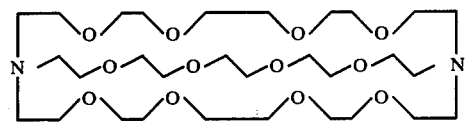

| Ex. No. | Glycolyl Chloride Reagent | Diamino-polyoxa-Reagent | Diamine Product A | Glycolyl Chloride Reagent | Bicyclic Product B |
|---|---|---|---|---|---|
| 80(b) | 78B | 79C | HN\|O O O O / O O O O\|NH | 1B | N\|O O O O / O O O O / O O O O\|N |
| 80(c) | " | " | " | 78B | N\|O O O O / O O O O / O O O O\|N |
| 80(d) | 13B | " | HN\| O O O / O O O O\|NH | 1B | HN\|O O O / O O O O / O O\|NH |
| 80(e) | 78B | 14C | " | " | |
|  | " | " | " | 13B | N\| O O O / O O O O / O O O\|N |
| 80(f) | 39 | 79C | HN\|O O O O / O\|NH | 78B | N\|O O O O / O / O O O O\|N |
| 80(g) |  |  | 80(a)-A | 39 | N\| O / O O / O O O O\|N |
| 80(h) |  |  | 80(f)-A<br>80(d)-A | 1B<br>39 | "<br>N\|O O O O / O / O O O\|N |
| 80(i) |  |  | 80(f)-A<br>45 | 13B<br>78B | "<br>N\| O / O / O O O O\|N |
| 80(j) |  |  | 33 | 78B | N\| S S / S S / O O O O\|N |
| 80(k) |  |  | 80(b)-A | 26B | N\|O O O O / O O O O / S S\|N |
| 80(l) |  |  | 29 | 78B | N\| S S / O O / O O O O\|N |
| 80(m) |  |  | 60B | 78B | N\| CH₃ CH₃ / N N / O O / O O O O\|N |

| Ex. No. | Glycolyl Chloride Reagent | Diaminopolyoxa- Reagent | Diamine Product A | Glycolyl Chloride Reagent | Bicyclic Product B |
|---|---|---|---|---|---|
| 80(n) | 66A | 79C | 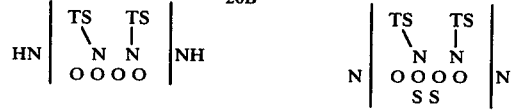 | 26B | |

EXAMPLE 81

Preparation of Polyalkylene glycols

Hexaethylene glycol and heptaethylene glycol are known compounds obtained by fractional distillation of commercially available polyethylene glycol. Alternatively, these compounds are prepared and described in procedures A and B hereinbelow.

A. Heptaethylene glycol

The requisite intermediate, triethylene glycol monobenzenesulfonate, is prepared by treating triethylene glycol with one equivalent of benzenesulfonyl chloride in pyridine and isolating the product according to known procedure.

Dissolve one equivalet of sodium in at least 5 equivalents of tetraethylene glycol and then add one equivalent of triethylene glycol monobenzenesulfonate. Heat the resulting solution at 100° to 150° C. until the elimination of sodium benzene sulfontate is substantially complete. Remove the insoluble sulfonate salt by filtration and fractionally distill the resultiing product in vacuo to obtain heptaethylene glycol as the higher boiling fraction.

B. Hexaethylene glycol

In a manner similar to that described in Example 81A above, dissolve one equivalent of sodium in at least 5 moles of triethylene glycol. Add one mole equivalent of triethylene glycol monobenzenesulfonate. Isolate and purify the resulting product in a manner similar to that described in Example 81 to obtain hexaethylene glycol.

C. Heptapropylene glycol

In a manner similar to that described in Example 81A, prepare tripropylene glycol monobenzenesulfonate by reaction of tripropylene glycol with benzene sulfonyl chloride in pyridine. Add one mole equivalent of tripropylene glycol with benzene sulfonate to a solution in which one mole equivalent of sodium is dissolved in at least 5 moles of tetrapropylene glycol. Heat the resulting solution at 100° to 150° C. until the elimination of benzenesulfonate is substantially complete. Isolate and purify the resulting product in a manner similar to that described in Example 81A to obtain heptaethylene glycol.

EXAMPLE 82

Preparation of polyglycolylchloride and polyoxadiamine starting compounds 82-1A In a manner similar to that described in Example 1, treat hexaethylene glycol with nitric acid and isolate and purify the resulting product in a manner similar to that described to obtain hexaglycolic acid. Treat the hexaglycolic acid with oxylyl chloride in anhydrous benzene in the presence of pyridine according to the procedure of Example 1B, then isolate and purify the resulting product in a manner similar to that described to obtain hexaglycolyl chloride (Compound 82-1A).

82-1B

In a manner similar to that described in Example 2, treat hexaethylene glycol with phosphorous tribromide then treat the hexaethylene glycol dibromide thereby produced with phthalimide and potassium hydroxide in ethanol then treat the thereby produced hexaethylene glycol diphthalimide with hydrazine in aqueous ethanol. Isolate and purify the resultant product in a manner similar to that described to obtain 1,17-diamino-3,6,9,12,15-pentaoxaheptadecane, (compound 82-1B).

82-(2A to 5A)

Similarly, treat each of the following propylenealkyleneglycols in a manner similar to that described in Example 1:

heptaethylene glycol;
tripropylene glycol;
tetrapropylene glycol;
heptapropylene glycol.

Isolate and purify each of the resulting products in a manner similar to that described in Example 1 to obtain respectively:

heptaglycolyl chloride (compound 82-2A);
tripropylene glycolyl chloride (compound 82-3A);
tetrapropylene glycolyl chloride (compound 82-4A);
heptapropylene glycolyl chloride (compound 82-5A);

82-(2B to 5B)

Treat each of the following polyalkylene glycols in a manner similar to that described in Example 2:

heptaethylene glycol;
tripropylene glycol;
tetrapropylene glycol;
heptapropylene glycol.

Isolate and purify each of the resulting products in a manner similar to that described in Example 2 to obtain respectively:

1,20-diamino-3,6,9,12,15,18-hexaoxaeicosane (compound 82-2B);
1,11-diamino-4,8-dioxaundecane (compound 82-3B);
1,15-diamino-4,8,12-trioxapentadecane (compound 82-4B);
1,27-diamino-4,8,12,16,20,24-hexaoxaheptacosane (compound 82-5B).

82-(6A, 7A)

Treat each of the following dichloroalkyl sulfides with thioglycolic acid in a manner similar to that described in Example 26:
di-(β-chloroethyl)sulfide; and ethylene bis-(β-chloroethyl sulfide).

Isolate and purify each of the resulting products in a manner similar to that described in Example 26 to obtain respectively:

tetrathiaglycolyl chloride (compound 82-6A);
pentathiaglycolyl chloride (compound 82-7A).

rides (or polythioglycolyl chlorides with each of the following polyheterodiaminoalkanes to obtain a polyheterodiazocyloalkane product A as indicated, followed by treatment thereof with a polyglycolyl chloride (or polythioglycolylchloride) in a manner similar to that described in Examples 5 and 6 to obtain a polyheterodiazabicycloalkane product B as indicated hereinbelow.

| Ex. No. | Glycolyl Chloride Reagent | Diamino-polyoxa-Reagent | Diamine Product A | Glycolyl Chloride Reagent | Bicyclic Product |
|---|---|---|---|---|---|
| 83(a) | 82-1A | 82-1B | HN[ooooo/ooooo]NH | 82-1A | N[ooooo/ooooo/ooooo]N |
| 83(b) | 82-2A | 82-2B | HN[oooooo/oooooo]NH | 82-2A | N[oooooo/oooooo/oooooo]N |
| 83(c) | 82-6A | 82-6B | HN[sss/sss]NH | 82-6A | N[sss/sss/sss]N |
| 83(d) | 82-7A | 82-7B | HN[ssss/ssss]NH | 82-7A | N[ssss/ssss/ssss]N |
| 83(e) | 82-3A | 82-3B | (structure) | 82-3A | (structure) |
| 83(f) | 82-4A | 82-4B | (structure) | 82-4B | (structure) |
| 83(g) | 82-5A | 82-5B | (structure) | 82-5B | (structure) |

82-(6B,7B)
Treat each of the following dichloroalkyl sulfides with cysteamine in a manner similar to that described in Example 27.

di-(β-chloroethyl) sulfide;
ethylene bis-(β-chloroethyl) sulfide) with cysteamine.

Isolate and purify each of the resulting products in a manner similar to that described in Example 27 to obtain respectively;

1,11,diamino-3,6,9-trithiaundecane (compound 82-6B);
1,14-diamino-3,6,9,12-tetrathiatetradecane (compound 82-7B).

EXAMPLE 83

Polyheterobicycloalkanes

In a manner similar to that described in Examples 3 and 4, treat each of the following polyglycolyl chlo-

EXAMPLE 84

4,13-Dialkyl-1,7,10,16-tetraoxa-4,13-diazacyclooctadecane

A. 4,13-Di-(n-decanoyl)-1,7,10,16-tetraoxa-4,13-diazacylooctadecane

In a manner similar to that described in Example 5, treat the cyclic diamine obtained in Example 4 and triethylamine in anhydrous benzene with a solution of n-decanoyl chloride (capryl chloride) in anhydrous benzene. Isolate and purify the resultant product in a manner similar to that described to obtain 4,13-di-(n-decanoyl)-1,7,10,16-tetraoxa-4,13-diazacyclooctadecane.

In the above procedure, by utilizing n-dodecanoyl chloride (lauroyl chloride) instead of n-decanoyl chloride, there is obtained 4,13-(n-dodecanoyl)-1,7,10,16-tetraoxa-4,13-diazacyclooctadecane.

B. 4,13-di-(n-decyl)-1,7,10,16-tetraoxa-4,13-diazacylooctadecane

In a manner similar to that described in Example 6, treat the cyclic diamide with boron hydride followed by treatment of the resulting diborane derivative with 6N-hydrochloric acid and thence treatment of the resulting dihydrochloride salt with tetramethylammonium hydroxide, or by chromatographing through a column of an anion exchange resin (Dowex) to obtain 4,13-di-(n-decyl)-1,7,10,16-tetraoxa-4,13-diazacyclooctadecane.

By treating 4,13-di-(n-dodecyl)-1,7,10,16-tetraoxa-4,13-diazacyclooctadecane with boron hydride in the above described manner, there is obtained 4,13-di-(n-dodecyl)-1,7,10,16-tetraoxa-4,13-diazacyclooctadecane.

Lithium aluminum hydride also may be used in this reduction in place of diborane.

EXAMPLE 85

Preparation of 1,2-Di-(chlorocarbonylmethoxymethyl)benzene

Treat o-xylene glycol with aqueous sodium hydride followed by monochloroacetic acid alkyl (methyl or ethyl) ester. Isolate and purify the resultant product in a manner similar to that described to obtain 1,2-di-(carboxymethoxymethyl)benzene, and by chromatography hydrolyze the resulting diacid diester in usual acid or base conditions.

In a manner similar to that described in Example 61B, treat 1,2-di-(carboxymethoxymethyl)benzene in anhydrous benzene with oxalyl chloride. Isolate and purify the resultant product in a manner similar to that described to obtain 1,2-di(chlorocarbonylmethoxymethyl)benzene.

EXAMPLE 86

Polyoxa-Polyazatricyclo[14,8,8,0$^{6,11}$]dotriaconta-6,8,10-trienes

A. 4,13,99,22,27,30-Hexaoxa-1,16-diazatricyclo[14,8,8,0$^{6,11}$]-dotriaconta-6,8,10-triene In a manner similar to that described in Examples 62 and 63, treat 1,7,10,16-tetraoxa-4,13-diazacyclooctadecane with 1,2-dichlorocarbonylmethoxymethyl benzene and triethylamine in anhydrous benzene utilizing high dilution techniques, followed by reduction of the diamide thereby obtained with diborane in anhydrous tetrahydrofuran and thence hydrolysis of the resultant diborane derivative with 6N hydrochloric acid and treatment of the resulting dihydrochloride salt with tetramethylammonium hydroxide or through a column of an anion exchange resin to obtain 4,13,19,22,27,30-hexaoxa-1,16-diazatricyclo[14,8,8,0$^{6,11}$]-dotriaconta-6,8,10-triene, having the following formula:

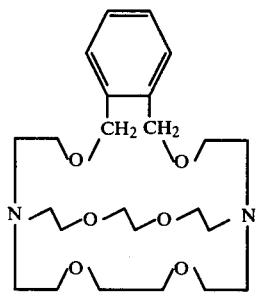

B. Treat the diamine obtained as described in Example 29 with 1,2-dichlorocarbonylmethoxymethyl benzene in a manner similar to that described in above Example 86A followed by treatment of the product thereby formed in a manner similar to that described in Example 86A to obtain 4,13,19,22-tetraoxa-27,30-dithia-1,16-diazatricyclo[14,8,8,0$^{4,13}$]dotriaconta-6,8,10-triene having the following formula:

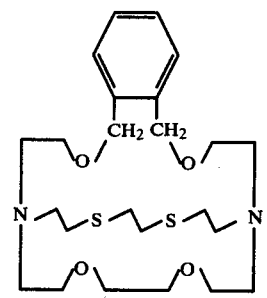

C. By subjecting the diamine obtained as described in Example 33 to the sequence of reactions described in above Example 86A, there is obtained 4,13-dioxa-19,22,27,30-tetrathia-1,16-diazatricyclo[14,8,8,0$^{6,11}$]dotriaconta-6,8,10-triene having the following formula:

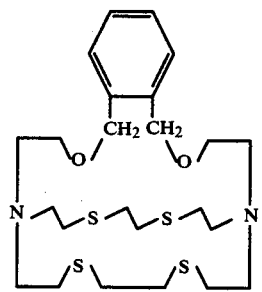

D. Similarly, treat the diamine obtained as described in Example 60 with 1,2-dichlorocarbonylmethoxymethyl benzene in a manner similar to that described in above Example 86A to obtain 27,30-dimethyl-4,13,19,22-tetraoxa-1,16,27,30-tetraazatricyclo-[14,8,8,0$^{6,11}$]dotriaconta-6,8,10-triene having the following formula:

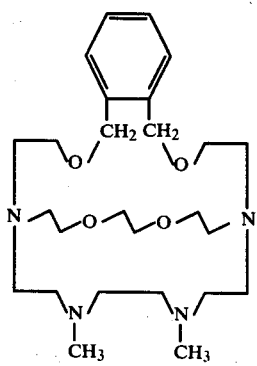

EXAMPLE 87

Cation Complexes of polyheterodiazabicycloalkane Macrocyclics

A. Listed below are some representative cation-containing compounds from which complexes have been formed with the macrocyclic compounds of this invention:

| | | | |
|---|---|---|---|
| KF | NaCl | CaBr$_2$ | TlCl |
| KCl | NaI | CaCl$_2$ | AgNO$_3$ |
| KBr | NaSCN | SrBr$_2$ | AgSCN |
| KI | Na$_2$SO$_4$ | SrCl$_2$ | Mg(OAc)$_2$ |
| KOH | Na$_2$(COO)$_2$ | BaCl$_2$ | LiSCN |
| KMnO$_4$ | RbCl | BaBr$_2$ | TlNO$_3$ |
| KNO$_3$ | NH$_4$SCN | BaSO$_4$ | TlHCOO |
| KBH$_4$ | RbSCN | CuCl$_2$ | Zn(BF$_4$)$_2$ |
| KSCN | CsSCN | CsCl | Pb(SCN)$_2$ |
| K$_2$(COO)$_2$ | NH$_4$I | Ba(SCN)$_2$ | Co(SCN)$_2$ |
| | | | TlNO$_3$ |

In addition to the cation-containing complexes specifically described in the foregoing examples, other useful complexes of the macrocyclic compounds of my invention include the following:

complexes of 4,11,17,20,25,28-hexaoxa-1,4-diazatricyclo[12,8,8,0$^{5,10}$]triaconta-5,7,9-triene (compound of Example 63), and of 4,11,17,24,29,32-hexaoxa-1,14-diazatetracyclo[12,12,8,0$^{5,10,18,23}$]tetratriaconta-5,7,9,18,20,22-hexaene (compound of Example 64) with LiSCN, NaSCN, KSCN, RbCl, CsCl, AgSCN, TlNO$_3$, CaBr$_2$, SrCl$_2$ and Ba(SCN)$_2$;

Complexes of 4,11,17,22-tetraoxa-1,14-diazatricyclo-[12,5,5,0$^{5,10}$]tetracosa-5,7,9-triene (compound of Example 65) with LiSCN, NaSCN, and KSCN;

Complex of 21,24-ditosyl-4,7,13,16-tetraoxa-1,10,21,24-tetraazabicyclo[8,8,8]hexacosane (compound of Example 68A) with silver nitrate (AgNO$_3$);

Complexes of 4,7,13,16-tetraoxa-1,10,21,24-tetraazabicyclo[8,8,8]hexacosane (compound of Example 68B) with NaSCN, KSCN, and CdCl$_2$;

Complex of 21,24-dioxa-1,4,7,10,13,16-hexaazabicyclo[8,8,8]hexacosane (compound of Example 70) with potassium thiocyanate (KSCN);

Complexes of 21,24-dimethyl-4,7,16,19-tetraoxa-1,10,21,24-tetraazabicyclo[8,8,8]hexacosane (compound of Example 76B) with KNO$_3$ and AgNO$_3$;

Complex of 13,16,21,24-tetramethyl-4,7-dioxa-1,10,13,16,21,24-hexaazabicyclo[8,8,8]hexacosane (compound of Example 77B) with potassium nitrate;

I claim:

1. A cation-containing complex of macrocyclic compound selected from the group consisting of the following formula I:

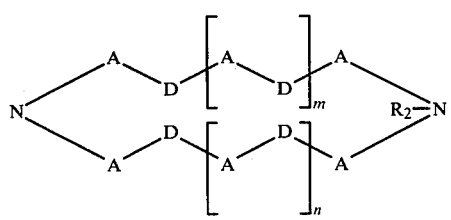

wherein R$_1$ and R$_2$ are members selected from the group consisting of hydrogen, a hydrocarbon radical having up to 12 carbon atoms, and together R$_1$ and R$_2$ form a grouping of the following formula II:

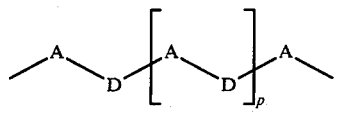

wherein each A is a hydrocarbon radical having from 2 to 8 carbon atoms;

each D is a member selected from the group consisting of oxygen, sulfur, a hydrocarbon radical having up to 8 carbon atoms, and =N—R (R being a member selected from the group consisting of hydrogen, a hydrocarbon radical having up to 12 carbon atoms, an aryl hydrocarbonsulfonyl radical having up to 12 carbon atoms, a lower alkoxycarbonyl radical, a lower alkoxycarbonylmethylene radical and a carboxymethylene radical);

at least two of aid D members being hetero-substituents selected from the group consisting of oxygen, sulfur and =N—R; and when each of R$_1$ and R$_2$ are members selected from the group consisting of hydrogen and a hydrocarbon radical, one of said two hetero-substituents is selected from the group consisting of oxygen and sulfur, the other of said two hetero-substituents is selected from the group consisting of oxygen and =N—R;

m, n and p are integers from 0 to 5;

and wherein said cation is a member selected from the group consisting of a compatible metal cation and a compatible ammonium cation.

2. A cation-containing complex according to claim 1 wherein each A is ethylene.

3. A cation-containing complex of claim 1 of a macrocyclic compound of formula I wherein R$_1$ and R$_2$ are hydrogen;

D is a member selected from the group consisting of sulfur and oxygen;

A is ethylene; and m, n and p are integers from 0 to 3.

4. A cation-containing complex of claim 1 of a macrocyclic compound of formula I wherein each D is oxygen;

each A is ethylene; and m, n and p are integers from 0 to 3.

5. A cation-containing complex of claim 1 of a macrocyclic compound of formula I wherein R$_1$ and R$_2$ together form the grouping

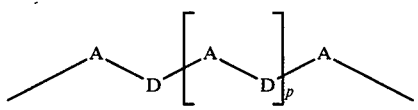

each A being ethylene; and m, n and p being integers from 0 to 3.

6. A cation-containing complex of claim 1 of a macrocyclic compound of formula I wherein R$_1$ and R$_2$ together form the grouping

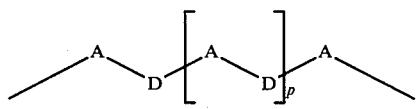

each D being a member selected from the group consisting of oxyen and sulfur;
each A being ethylene; and
m, n and p being integers from 0 to 3.

7. A cation-containing complex of claim 1 of a macrocyclic compound of formula I wherein R₁ and R₂ together form the grouping

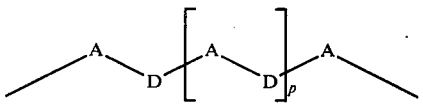

each D being a member selected from the group consisting of oxygen and =N—R (R being a member selected from the group consisting of hydrogen and a hydrocarbon radical having up to 12 carbon atoms);
each A being ethylene; and
m, n and p being integers from 0 to 2.

8. A cation-containing complex of clam 1 of a compound of formula I wherein R₁ and R₂ together form the grouping

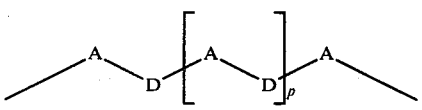

each D is oxygen;
each A is ethylene; and
m, n and p are integers from 0 to 2.

9. A compound according to claim 1 which is the potassium thiocyanate complex of 1,7,10,16-tetraoxa-4,13-diazacyclooctadecane.

10. A compound according to claim 1 which is the cupric chloride complex of 1,7,10,16-tetraoxa-4,13-diazacyclooctadecane.

11. A compound according to claim 1 which is the rubidium thiocyanate complex of 4,7,13,16,21,24-hexaoxa-1,10-diazabicyclo-[8,8,8]hexacosane 12. A compound according to claim 1 which is the barium chloride complex of 4,7,13,16,21,24-hexaoxa-1,10-diazabicyclo[8,8,8]hexacosane.

13. A compound according to claim 1 which is the potassium hydroxide complex of 4,7,13,16,21,24-hexaoxa-1,10-diazabicyclo[8,8,8]hexacosane.

14. A compound according to claim 1 which is the thallium formate complex of 4,7,13,16,21,24-hexaoxa-1,10-diazabicyclo[8,8,8]hexacosane.

15. A compound according to claim 1 which is the calcium thiocyanate complex of 4,7,13,16,21,24-hexaoxa-1,10-diazabicyclo[8,8,8]exacosane.

16. A compound according to claim 1 which is the zinc borofluoride complex of 4,7,13,16,21,24-hexaoxa-1,10-diazabicyclo[8,8,8]hexacosane.

17. A compound according to claim 1 which is the lead thiocyanate complex of 4,7,13,16,21,24-hexaoxa-1,10-diazabicyclo[8,8,8]hexacosane.

18. A compound according to claim 1 which is the caesium thiocyanate complex of 4,7,10,16,19,22,27,30,33-nonoxa-1,13-diazabicyclo[11,11,11]pentatriacontane.

19. A compound according to claim 1 which is the potassium thiocyanate complex of 4,7,13,16,21-pentaoxa-1,10-diazabicyclo[8,8,5]tricosane.

20. A compound according to claim 1 which is the cobalt thiocyanate complex of 4,7,13,16,21-pentaoxa-1,10-diazabicyclo[8,8,5]tricosane.

21. A compound according to claim 1 which is the barium chloride complex of 4,7,13,16,21-pentaoxa-1,10 diazabicyclo[8,8,5]tricosane.

22. A compound according to claim 1 which is the nickel borofluoride complex of 4,7,13,16,21-pentaoxa-1,10-diazabicyclo[8,8,5]tricosane.

23. A compound according to claim 1 which is the cupric borofluoride complex of 4,7,13,16,21-pentaoxa-1,10-diazabicyclo8,8,5]tricosane.

24. A compound according to claim 1 which is the barium thiocyanate complex of 4,7,10,16,19,24,27-heptaoxa-1,13-diazabicyclo[8,8,11]nonacosane.

25. A compound according to claim 1 which is the potassium hydroxide complex of 4,7,13,18-tetraoxa-1,10-diazabicyclo[5,5,8]eicosane.

26. A compound according to claim 1 which is a cation-containing complex of 4,7,13,16,21,24-hexaoxa-1,10-diazabicyclo[8,8,8]hexacosane wherein said cation is strontium.

27. A compound according to claim 1 which is the cation-containing complex of 4,11,17,20,25,28-hexaoxa-1,4-diazatricyclo [12,8,8,0$^{5,10}$]triaconta-5,7,9-triene with a member selected from the group consisting of LiSCN, NaSCN, KSCN, RbCl, CsCl, AgSCN, TlNO₃, CaBr₂, SrCl₂ and Ba(SCN)₂.

28. A compound according to claim 1 which is the cation-containing complex of 4,11,17,24,29,32-hexaoxa-1,14-diazatetracyclo [12,12,8,0$^{5,10,18,25,23}$]tetratriaconta-5,7,9,18,20,22-hexaene with a member selected from the group consisting of LiSCN, NaSCN, KSCN, RbCl, CsCl, AgSCN, TlNO₃, CaBr₂, SrCl₂ and Ba(SCN)₂.

29. A compound according to claim 1 which is the cation-containing complex of 4,11,17,22-tetraoxa-1,14-diazatricyclo[12,5,5,0$^{5,10}$]tetracosa-5,7,9-triene with a member selected from the group consisting of LiSCN, NaSCN, and KSCN.

30. A compound according to claim 1 which is the silver nitrate complex of 21,24-ditosyl-4,7,13,16-tetraoxa-1,10,21,24-tetraazabicyclo[8,8,8]hexacosane.

31. A compound according to claim 1 which is the cation-containing complex of 4,7,13,16-tetraoxa-1,10,21,24-tetraazabicyclo[8,8,8]hexacosane with a member selected from the group consisting of NaSCN, KSCN, and CdCl₂.

32. A compound according to claim 1 which is the potassium thiocyanate complex of 21,24-dioxa-1,4,7,10,13,16-hexaazabicyclo[8,8,8]hexacosane.

33. A compound according to claim 1 which is the cation-containing complex of 21,24-dimethyl-4,7,16,19-tetraoxa-1,10,21,24-tetraazabicyclo[8,8,8]hexacosane with a member selected from the group consisting of potassium nitrate and silver nitrate.

34. A compound according to claim 1 which is the potassium nitrate complex of 13,16,21,24-tetramethyl-4,7 dioxa-1,10,13,16,21,24-hexaazabicyclo[8,8,8]hexacosane.

35. A compound according to claim 1 which is the potassium chloride complex of 4,7,13,16,21,24-hexaoxa-1,10-diazabicyclo[8,8,8]hexacosane.

36. A macrocyclic compound according to claim 1 which is a cation-containing complex of a macrocyclic compounds wherein D is oxygen; A is ethylene; R₁ and R₂ are each a hydrocarbon radical having up to 12 carbon atoms, and m and n are the integer 1.

37. The process for the preparation of the potassium hydroxide complex of 4,7,13,16,21,24-hexaoxa-1,10-diazabicyclo[8,8,8]hexacosane which comprises admixing 4,7,13,16,21,24-hexaoxa-1,10-diazabicyclo[8,8,8]hexacosane with potassium hydroxide in tetrahydrofuran.

38. The process for the preparation of the potassium hydroxide complex of 4,7,13,18-tetraoxa-1,10-diazabicyclo[5,5,8]eicosane which comprises admixing 4,7,13,18-tetraoxa-1,10-diazabicyclo[5,5,8]eicosane with potassium hydroxide in tetrahydrofuran.

39. The process which comprises treating a cation-containing complex of a compound of formula I as defined in claim 1, with a member selected from the group consisting of an acid and a quaternizing agent and, when said compound of formula I is a bicyclic compound wherein $R_1$ and $R_2$ form a grouping of formula II therein, with a per-acid, whereby said complex is dissociated and there is obtained a salt containing said cation and an acid addition or a quaternary ammonium salt, respectively, of said macrocyclic compound of formula I, claim 1, or an N-oxide salt of said bicyclic compound of formula I, claim 1.

40. The process of claim 39 wherein said cation-containing complex is treated with an acid whereby there is obtained an acid addition salt of said compound of formula I, claim 1, and a salt containing said cation.

41. The process of claim 40 wherein said cation-containing complex is treated with hydrochloric acid whereby there is obtained a hydrogen chloride acid addition salt of said compound of formula I, claim 1, and a salt of said cation.

42. A cation-containing complex of claim 1 wherein said cation is a compatible metal cation selected from the group consisting of $Li^+$, $Na^+$, $K^+$, $Rb^+$, $Cs^+$, $Mg^{++}$, $Ca^{++}$, $Sr^{++}$, $Ba^{++}$, $NH_4^+$, $Co^{++}$, $Ni^{++}$, $Cu^{++}$, $Zn^{++}$, $Ag^+$, $Cd^{++}$, $Pb^{++}$, and $Tl^+$.

* * * * *

UNITED STATES PATENT AND TRADEMARK OFFICE
CERTIFICATE OF CORRECTION

PATENT NO. : 4,156,683
DATED : May 29, 1979
INVENTOR(S) : Jean-Marie Lehn

It is certified that error appears in the above-identified patent and that said Letters Patent are hereby corrected as shown below:

Column 2, line 44, at left of Formula I, "[structure]" should read ---[structure]---. Column 7, line 15, bottom of formula B, "$(m +)Z\ominus$" should read ---$(m + 3)Z\ominus$---. Columns 9 and 10, fourth formula, top line at left, "[structure]" should read ---[structure]---. Column 13, second formula, "[structure]" should read ---[structure]---. Column 21, last line, "(1) $A + - \rightleftarrows AM^+$" should read ---(1) $A + M^+ \rightleftarrows AM^+$---. Column 22, line 22, "$K_1 = [AH^+]/[AH_2^{++}]$" should read ---$K_1 = [AH^+][H^+]/[AH_2^{++}]$---.

Column 22, line 27, "$AMH^{230} \rightleftarrows$" should read ---$AMH^{2+} \rightleftarrows$---.

UNITED STATES PATENT AND TRADEMARK OFFICE
CERTIFICATE OF CORRECTION

PATENT NO. : 4,156,683

DATED : May 29, 1979

INVENTOR(S) : Jean-Marie Lehn

It is certified that error appears in the above-identified patent and that said Letters Patent are hereby corrected as shown below:

Column 23, lines 22-28 in second table, "Cation   $K_s$   $-pK_s$"

| Cation | $K_s$ | $-pK_s$ |
|---|---|---|
| $Li^+$ | $2.7 \times 10^2$ | 2.43 |
| $Na^+$ | $1.9 \times 10^5$ | 5.28 |
| $K^+$ | $8.2 \times 10^3$ | 3.91 |
| $Rb^+$ | $3.-5 \times 10^2$ | 2.54 |
| $Cs^+$ | $<10$ | $<1.5$ | should read ---Cation   $K_s$   $-pK_s$---

| Cation | $K_s$ | $-pK_s$ |
|---|---|---|
| $Li^+$ | $2.7 \times 10^2$ | 2.43 |
| $Na^+$ | $1.9 \times 10^5$ | 5.28 |
| $K^+$ | $8.2 \times 10^3$ | 3.91 |
| $Rb^+$ | $3.5 \times 10^2$ | 2.54 |
| $Cs^+$ | $<10^{1.5}$ | $<1.5$ |

Column 23, line 35, "...$LiCl(\frac{N}{10})$" should read ---$NMe_4 Br (\frac{N}{10})$---.

Column 24, line 40, "$Mg^{++} <10^2 >2$" should read ---$Mg^{++} < 10^2 <2$---. Column 33, line 22, "of 255 g." should read ---of 2.45 g.---. Column 33, line 43, "4,7,10,16,18,24,27" should read ---4,7,10,16,19,24,27---. Column 41, line 37, "Example 42" should read ---Example 41---. Column 42, line 29, "Example 30" should read ---Example 39---. Column 44, line 56,

UNITED STATES PATENT AND TRADEMARK OFFICE
CERTIFICATE OF CORRECTION

PATENT NO. : 4,156,683

DATED : May 29, 1979

INVENTOR(S) : Jean-Marie Lehn

It is certified that error appears in the above-identified patent and that said Letters Patent are hereby corrected as shown below:

"the KSCW-complex" should read ---the KSCN-complex---. Column 49, line 57, "60 ml. 6H" should read ---60 ml. 6N---. Column 50, line 6, "4,11,17,24,32" should read ---4,11,17,24,29,32---. Column 50, line 24, "$[12,0,0^{8,13}]$" should read ---$[12,8,0^{8,13}]$--- Column 52, line 4, "absolute ethanol methanol" should read ---absolute methanol---. Column 55, line 59, "dioxahydexaa-" should read ---dioxahexaaza---. Column 58, line 25, "Examples 66B through 55E" should read ---Examples 66B through 66E---. Column 58, line 66, "($CH_2COOOC_2H_5$)" should read ---($CH_2COOC_2H_5$)---. Column 60, line 1, "O-($CH_2OCH_2COCl$" should read ---O-($CH_2$)$_2OCH_2COCl$--- Column 60, line 61, "4,7,13,16,21,24,2,30" should read ---4,7,13,16,21,24,27,30---. Column 62, lines 12 and 13, "and N/oooo/N is" should read ---and N/oooo/N is---.

Column 62, lines 29-31, the third compound listed under Bicyclic Product B, "HN/ooo/NH" should read ---N/ooo/N---.

Column 67, line 40, "A. 4,13,99,22,27,30" should read ---A. 4,13,19,22,27,30---. Column 68, line 46, "Example 60 with" should read ---Example 60B with---. Column 69, claim 1,

UNITED STATES PATENT AND TRADEMARK OFFICE
CERTIFICATE OF CORRECTION

PATENT NO. : 4,156,683                      Page 4 of 4

DATED : May 29, 1979

INVENTOR(S) : Jean-Marie Lehn

It is certified that error appears in the above—identified patent and that said Letters Patent are hereby corrected as shown below:

lines 59-61, " 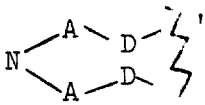 " should read ---  .

Column 72, claim 28, line 32, "$[12,12,8,0^{5,10,18,25,23}]$" should read ---$[12,12,8,0^{5,10,18,23}]$---.

Signed and Sealed this

*Thirtieth* Day of *December 1980*

[SEAL]

*Attest:*

SIDNEY A. DIAMOND

*Attesting Officer*        *Commissioner of Patents and Trademarks*